United States Patent [19]

Machida et al.

[11] Patent Number: 5,373,000
[45] Date of Patent: Dec. 13, 1994

[54] 7BETA-(THIADIAZOLYL)-2-IMINOACETAMIDO-3CEPHEM COMPOUNDS

[75] Inventors: Yoshimasa Machida; Takashi Kamiya; Shigeto Negi; Toshihiko Naito; Yuuki Komatu; Seiichiro Nomoto; Isao Sugiyama; Hiroshi Yamauchi, all of Ibaraki, Japan

[73] Assignee: Eisai Co., Ltd., Tokyo, Japan

[21] Appl. No.: 861,717

[22] Filed: Apr. 1, 1992

Related U.S. Application Data

[63] Continuation of Ser. No. 336,558, Apr. 11, 1989, abandoned, which is a continuation-in-part of Ser. No. 94,487, Aug. 21, 1987, abandoned.

[30] Foreign Application Priority Data

| Dec. 26, 1985 | [JP] | Japan | 60-291836 |
| Feb. 24, 1986 | [JP] | Japan | 61-37449 |
| Oct. 2, 1986 | [JP] | Japan | 61-233356 |
| Apr. 12, 1988 | [JP] | Japan | 63-88117 |

[51] Int. Cl.$^5$ ............... C07D 501/34; N61K 31/545
[52] U.S. Cl. ........................... 514/202; 514/203; 514/205; 514/204; 540/222; 540/225; 540/227
[58] Field of Search ............ 540/222, 225, 227; 514/202, 203, 205

[56] References Cited

U.S. PATENT DOCUMENTS

| 4,464,368 | 8/1984 | O'Callaghan | 514/202 |
| 4,486,586 | 12/1984 | Narita | 540/222 |
| 4,604,456 | 8/1986 | Takaya et al. | 540/222 |
| 4,751,295 | 6/1988 | Oka | 540/222 |
| 4,822,785 | 4/1989 | Ishibashi et al. | 514/202 |
| 4,921,850 | 5/1990 | Kamiya et al. | 514/202 |

FOREIGN PATENT DOCUMENTS

| 85-03938 | 9/1985 | WIPO | 540/222 |
| 87-03875 | 7/1987 | WIPO | |

OTHER PUBLICATIONS

PCT Gazette–Section 1, No. 14 (1987) abstracting WO 87/03875.

Primary Examiner—Donald G. Daus
Attorney, Agent, or Firm—Wenderoth, Lind & Ponack

[57] ABSTRACT

A cephalosporin derivative represented by the formula:

wherein $R_1$ represents a lower alkyl group, and A is selected from:

a group of the following formula:

$$-\overset{R_2}{\underset{R_3}{\overset{|}{N}}}-R_4$$

where $R_2$ and $R_3$ are the same or different lower alkyl group, $R_4$ represents a substituted lower alkyl or amino group;

a group which may be substituted and which is represented by the following formula:

(Abstract continued on next page.)

-continued
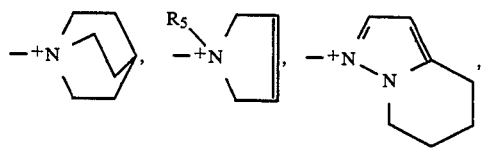 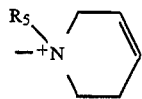
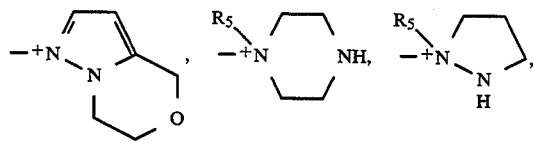 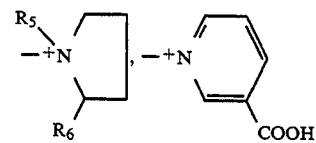
where $R_5$ represents a lower alkyl group; or a group of the following formula:
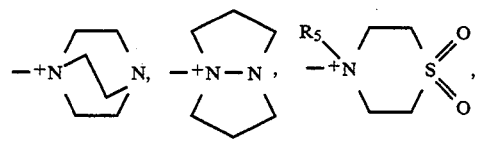
where $R_5$ is as defined above, $R_6$ represents a hydroxyl lower alkyl or carboxyl group, or its pharmacologically acceptable salt, and a process for preparing the same, as well as an antibacterial agent containing the same.
3 Claims, No Drawings

7BETA-(THIADIAZOLYL)-2-IMINOACETAMIDO-3CEPHEM COMPOUNDS

This application is a continuation of now abandoned application Ser. No. 07/336,558 filed Apr. 11, 1989, which is continuation-in-part of now abandoned application Ser. No. 07/094,487 filed Aug. 21, 1987.

OBJECT OF THE INVENTION

The present invention relates to novel cephalosporin derivatives useful for anti-bacterial agents, or their pharmacologically acceptable salts, and a process for the preparation thereof.

Cephalosporin derivatives having a quaternary ammonio group, similar to compounds of the present invention, have been conventionally known from Japanese Patent Application Laid-open Nos. 174387/83; 198490/83; 130295/84; 219292/84; 97983/85; 197693/85, etc. However, a very satisfactory compound has not been provided in respect of a compound effective against both Gram-positive bacteria and Gram-negative bacteria (particularly, Pseud. aeruginosa).

The present inventors have found that the compounds of the present invention exhibit excellent anti-bacterial activities against both Gram-positive bacteria and Gram-negative bacteria (Pseud. aeruginosa), and have thus accomplished the present invention.

It is therefore an object of the present invention to provide a novel compound useful for an anti-bacterial agent and a process for the preparation thereof as well as a medicine containing the same.

CONSTRUCTION OF THE INVENTION

The present invention relates to cephalosporin derivatives represented by the formula:

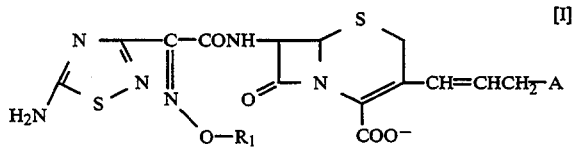

wherein $R_1$ represents a lower alkyl group, and A is selected from:
a group of the following formula:

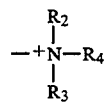

where $R_2$ and $R_3$ are the same or different lower alkyl group, $R_4$ is a lower alkyl group substituted with a group selected from the group consisting of a carbamoyl, carboxyl, lower alkyl-substituted amino, mercapto, lower alkanoyl, hydroxyl, and hydrazinocarbonyl group, or is a lower alkyl substituted with a 5-membered heterocyclic radical which may have a substituent, or is an amino group;

a group which may be substituted with a radical selected from carbamoyl, lower alkyldithio, lower alkyl, sulfamoyl, formimidoyl and carboxyl groups and which is represented by the following formula:

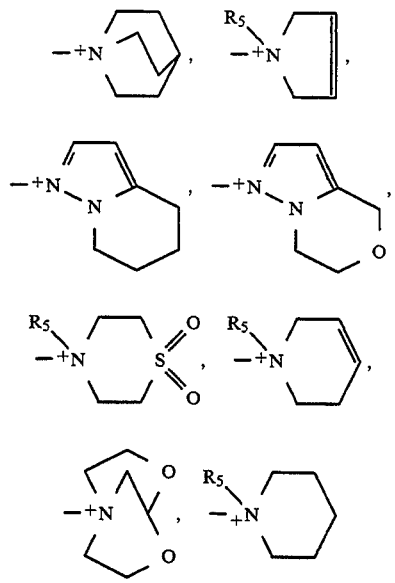

where $R_5$ represents a lower alkyl, hydroxy lower alkyl or carbamoyl lower alkyl group; or
a group of the following formula:

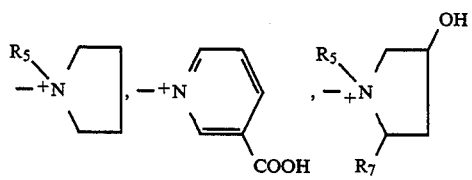

where $R_5$ is as defined above, and $R_6$ represents a hydroxyl lower alkyl or carboxyl group, and $R^7$ represents hydrogen atom or a hydroxy lower alkyl group, or its pharmacologically acceptable salt.

The lower alkyl groups represented by $R_1$ in the above formula (I) include $C_1$-$C_4$ groups such as methyl, ethyl, n-propyl, i-propyl, n-butyl, sec-butyl, t-butyl, and the like.

Examples of the lower alkyl groups defined for A in the formula (I) are those similar to the above examples of the lower alkyl groups represented by $R_1$.

Examples of the lower alkanoyl groups represented by $R_2$, $R_3$ and $R_4$ are acetyl, propanoyl, and the like.

The 5-membered heterorings in the 5-membered heterocyclic lower alkyl groups, which may have a substituent or substituents, represented by $R_4$ include thiazolyl, pyrazolyl, oxadiazolyl, imidazolyl, furyl, isothiazolyl, iso-oxazolyl, thiadiazolyl, thienyl, pyrrolyl, tetrazolyl, triazolyl, and the like. The substituents on these 5-membered heterorings include amino; carboxyl; lower alkyl groups such as methyl, ethyl, n-propyl, i-propyl, n-butyl, sec-butyl, t-butyl, etc.; carboxy lower alkyl groups such as carboxymethyl, carboxyethyl, etc.; carbamoyl; hydroxyl; lower alkyl substituted amino groups such as dimethylamino and diethylamino, etc.; and hydroxy lower alkyl groups such as hydroxymethyl and hydroethyl, etc.

Illustrative of the groups represented by A are:

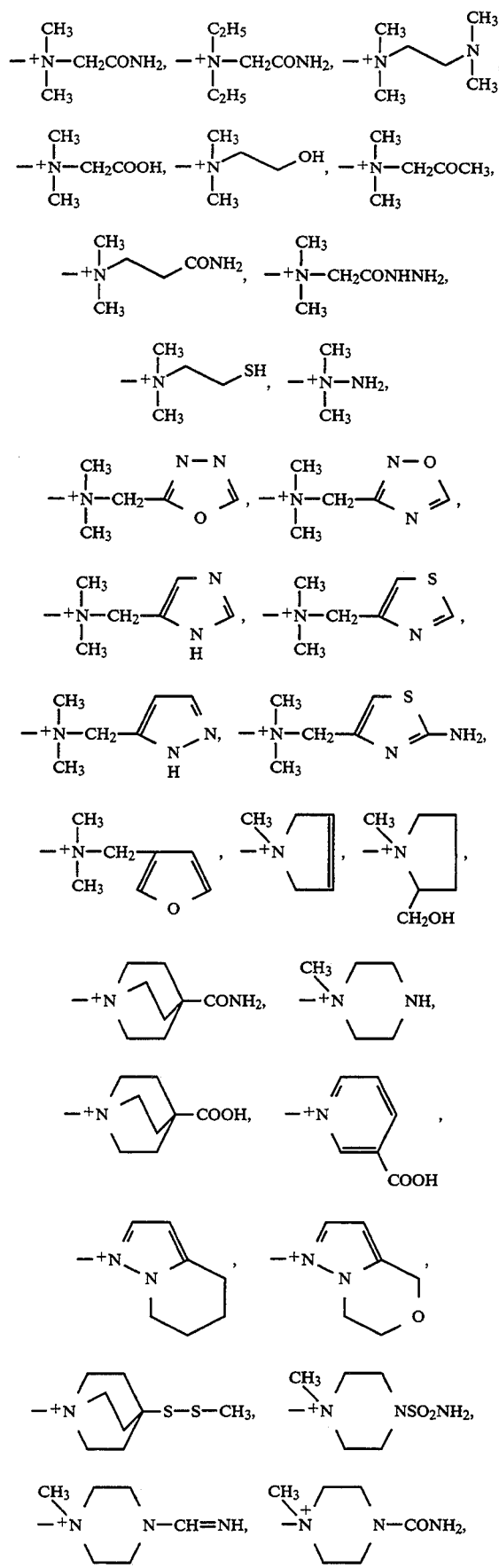
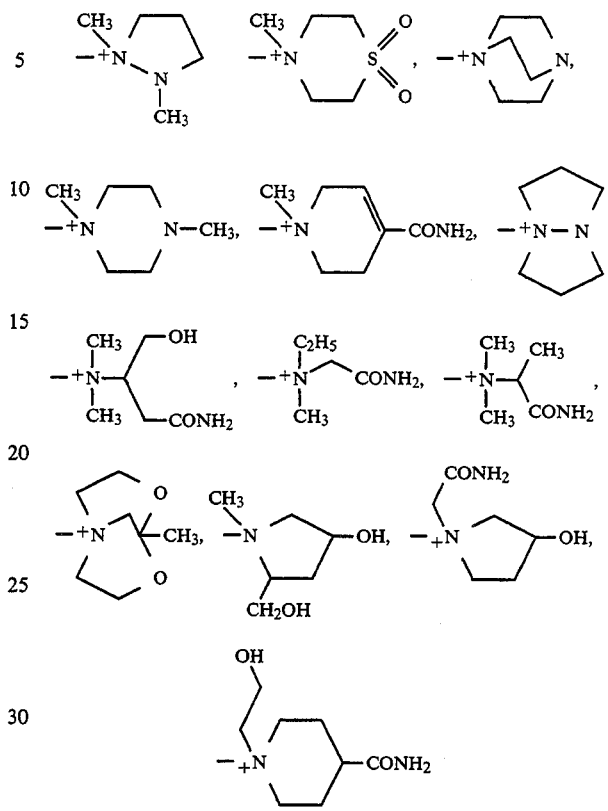

The pharmacologically acceptable salts of the compounds represented by the formula (I) include medicinally acceptable salts, for example, alkali metal salts such as sodium, potassium salts, etc.; alkaline earth metal salts such as calcium, magnesium salts, etc.; inorganic acid salts such as hydrochlorides, hydrobromides, hydroiodides, sulfates, carbonates, bicarbonates, etc.; organic carboxylic salts such as acetates, maleates, lactates, tartrates, etc.; organic sulfonates such as methane sulfonates, benzene sulfonates, toluene sulfonates, etc.; salts of amino acids such as salts of arginine, lysine, serine, aspartic acid and glutamic acid, etc.; and salts of amines such as salts of trimethylamine, triethylamine, pyridine, procaine, picoline, dicyclohexylamine, N,N'-dibenzylethylene diamine, N-methylglucamine, diethanolamine, triethanolamine, tris-(hydroxymethylamine) methane and phenethylbenzylamine, etc.

For steric configuration of the following moiety of the compound represented by the formula (I) according to the present invention, there are syn-isomer (Z) and anti-isomer (E).

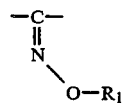

The present invention includes both of such isomers, but the syn isomers are preferred from the viewpoint of antibacterial activities.

The compounds according to the present invention may be prepared in accordance with the following processes.

The compound of the formula (I) or the pharmacologically acceptable salt thereof can be provided by reacting a compound represented by the formula:

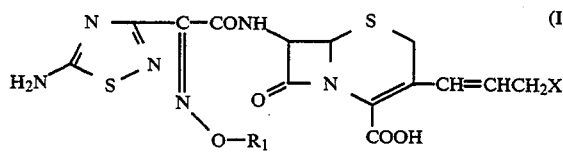

wherein $R_1$ is as defined above, and X is halogen atom, a compound with the amino and/or carboxyl group(s) of the compound being protected by a protective group, or a salt of one of these compounds, with a compound or its salt represented by the formula:

$$A' \qquad (III)$$

wherein A' is an amine corresponding to A, and, if necessary, removing the protective group.

The halogen atoms represented by X in the above formula (II) include iodine, bromine and chlorine atoms. The group A' is a tertiary amine corresponding to the group A in the above formula (I).

The reaction may be carried out at a temperature in a range of $-10°$ C. to $60°$ C., preferably $0°$ C. to $40°$ C. Preferable reaction solvents are anhydrous organic solvents. The organic solvents which may be used include lower alkylnitrides such as acetonitrile and propyonitrile etc.; halogenated lower alkanes such as chloromethane, dichloromethane and chloroform etc.; ethers such as tetrahydrofurane, dioxane and ethylether etc.; amides such as N,N-dimethylformamide etc.; esters such as ethyl acetate etc.; ketones such as acetone; and hydrocarbons such as benzene etc., or the mixtures of these solvents.

The removal of the protective group may be carried out in a usual manner, for example, by hydrolysis or reduction and the like, depending upon the type of the protective group used.

For the protective groups for the amino and carboxyl groups in the salts of the compounds of the formulae (II) and (III) and in the compounds of the formula (II), any groups usually employed can be used unless they will prevent the aforesaid reaction.

Illustrative of the protective groups for the amino groups are, for example, formyl, acetyl, chloroacetyl, dichloroacetyl, t-butoxycarbonyl, benzyloxycarbonyl, trityl, p-methoxybenzyl, and diphenylmethyl groups etc. Illustrative of the protective groups for the carboxyl groups are p-methoxybenzyl, p-nitrobenzyl, t-butyl, methyl, 2,2,2-trichloroethyl, diphenylmethyl and pivaloyloxymethyl groups etc. It is convenient to use a silylating agent such as bis-(trimethylsilyl) acetoamide, N-methyl-N-(trimethylsilyl) acetoamide, and N-methyl-N-trimethylsilyl-trifluoroacetoamide etc., because they can concurrently protect both the amino and carboxyl groups.

The salts of the compounds represented by the formulae (II) and (III) can be selected from the group consisting of alkali metal salts such as sodium and potassium salts etc.; alkaline earth metal salts such as calcium and magnesium salts etc.; ammonium salts; inorganic acid salts such as hydrochlorides, hydrobromides, sulfates, carbonates, hydroiodides and bicarbonates etc.; organic carboxylic acid salts such as acetates, trifluoroacetates, maleates, lactates and tartrates; organic sulfonates such as methane sulfonates, benzene sulfonates and toluene sulfonates etc.; salts of amine such as salts of trimethylamine, triethylamine, pyridine, procaine, picoline, dicyclohexylamine, N,N'-dibenzylethylene diamine, N-methylglucamine, diethanolamine, triethanolamine, tris-(hydroxymethylamine)methane and phenethylbenzylamine etc.; and salts of amino acids such as salts of arginine, aspartic acid, lysine, glutamic acid and serine, etc.

The compounds according to the present invention have strong anti-bacterial activities against Gram-negative bacteria and Gram-positive bacteria and are useful as anti-bacterial agents.

Any of the following compounds according to the present invention had an acute toxicity value [$LD_{50}$ (intravenous injection into mice)] of 3,000 mg/kg or more:

7β-[2-(5-Amino-1,2,4-thiadiazol-3-yl)-(Z)-2-methoxyiminoacetamide]-3-[(E)-3-[(1R-carbamoyl-2-hydroxyethyl) dimethylammonio]-1-propenyl]-3-cephem-4-carboxylate;

7β-[2-(5-Amino-1,2,4-thiadiazol-3-yl)-(Z)-2-methoxyiminoacetamide]-3-[(E)-3-(carbamoylmethylethylmethylammonio)-1-propenyl]-3-cephem-4-carboxylate; and 7β-[2-(5-Amino-1,2,4-thiadiazol-3-yl)-(Z)-2-methoxyiminoacetamide]-3-[(E)-3-(5-aza-1-methyl-2,8-diozabicyclo[3,3,1]nonan-5-io)-1-propenyl]-3-cephem-4-carboxylate.

7β-[2-(5-Amino-1,2,4-thiadiazol-3-yl)-(Z)-2-methoxyiminoacetamide]-3-[(E)-3-(carbamoylmethyl-dimethylammonio)-1-propene-1-yl]-3-cephem-4-carboxylate;

7β-[2-(5-Amino-1,2,4-triadiazol-3-yl)-(Z)-2-methoxyiminoacetamide]-3-[(E)-3-[(1,3,4-oxadiazol-2-yl)methyldimethylammonio]-1-propene-1-yl]-3-cephem-4-carboxylate;

and

7β-[2-(5-Amino-1,2,4-thiadiazol-3-yl)-(Z)-2-methoxyiminoacetamide]-3-[(E)-3-(1,4-dimethyl-1-piperazinio)-1-propene-1-yl]-3-cephem-4-carboxylate.

In using the compounds according to the present invention as injections, they may be intraveneously or intramuscularly administered in an amount of 100 mg to 10 g divided 1 to 4 times per day. It should be noted that the dosages may be increased or decreased depending upon the age and condition of the patient.

The injections can be produced in a usual manner. For example, the compound according to the present invention may be dissolved in distilled water in the presence of an isotonic agent, a dissolving assistant or the like as required, thereby providing an injection. Alternatively, the compound may be charged into a vial or the like in a form of a powder to form an injection of a type which may be dissolved when it is to be used. The injection of this type may be used by dissolving it into a medium such as an injecting distilled-water, a physiological saline solution, a glucose injecting liquid, or an amino acid carrier liquid when it is to be administered.

The present invention will now be described in more detail by way of experiments and examples.

EXPERIMENT 1

Synthesis of Source Compound p-Methoxybenzyl 7β-[2-(5-tritylamino-1,2,4-thiadiazol-3-yl)-(Z)-2-methoxyiminoacetamido]-3-chloromethyl-3-cephem-4-carboxylate

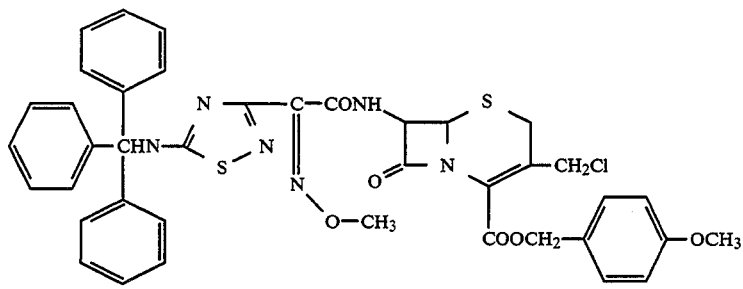

100 G of 2-(5-tritylamino-1,2,4-thiadiazol-3-yl)-(Z)-2-methoxyimino acetic acid were dissolved in 1 l of dimethylformamide, and to which 121.7 g of p-methoxybenzyl 7β-amino-3-chloromethyl-3-cephem-4-carboxylate p-toluene sulfonate, 22.77 g of triethylamine and 139.6 g of N-ethyl-N'-3-dimethylaminopropyl carbodiimide hydrochloride were added under ice-cooling, and the whole was stirred at the same temperature for 8 hours. After addition of 4 l of ethyl acetate to the reaction solution, it was washed with water, a saturated brine, a saturated aqueous sodium hydrogen carbonate, a saturated brine, 1 N hydrochloric acid and a saturated brine, in order. Anhydrous magnesium sulfate was added to the product to dry the same. Thereafter, the solvent was distilled off under vacuum. The residue was purified with a silica gel column chromatography (elution: chloroform) to yield 115 g of the objective compound.

EXPERIMENT 2

Synthesis of Source Compound p-Methoxybenzyl 7β-[2-(5-tritylamino-1,2,4-thiadiazol-3-yl)-(Z)-2-methoxyiminoacetamido]-3-iodomethyl-3-cephem-4-carboxylate

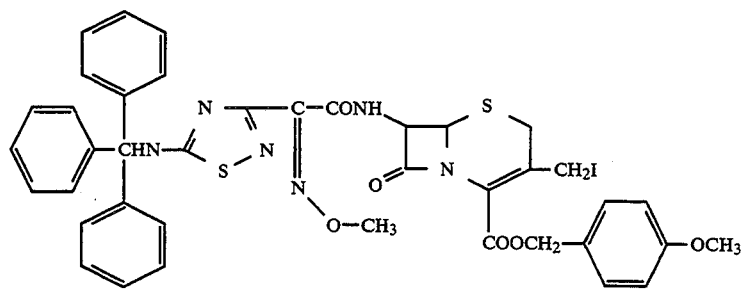

60 G of the compound obtained in the Experiment 1 were dissolved in 1.2 l of methylethylketone, and 56.5 g of methyliodide were added thereto, and the whole was stirred at the room temperature for one hour. The solvent was distilled off and the residue was dissolved in ethyl acetate, followed by washing with water, a saturated aqueous sodium thiosulfate solution and a saturated brine in order and it was dried with adding anhydrous magnesium sulfate. The resulting product was concentrated under reduced pressure. n-Hexane was added to the concentrate to collect the resulting precipitates by filtration, and 61.0 g of the objective compound were obtained.

EXPERIMENT 3

Synthesis of source compound p-Methoxybenzyl-7β-[2-(5-tritylamino-1,2,4-thiadiazol-3-yl)-(Z)-2-methoxyiminoacetamide]-3-triphenylsulfonyomethyl-3-cephem-4-carboxylate iodide

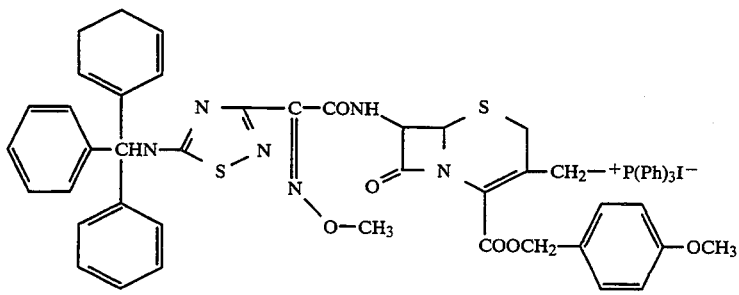

9.54 G of the compound obtained in the Experiment 2 were dissolved in 190 ml of benzene, and 5.64 g of triphenylphosphine were added thereto. The mixture was stirred at the room temperature for one hour. To this reaction solution were added dropwise 100 ml of n-hexane, and the resulting precipitate was collected by filtration. The precipitate was then washed with a liquid mixture of benzene-n-hexane (1:1) and n-hexane to yield 11.30 g of the objective compound.

uct. This product was purified by silica gel column chromatography (elution: chloroform) to yield 7.73 g of the objective compound.

EXPERIMENT 5

Synthesis of Source Compound p-Methoxybenzyl 7β-[2-(5-tritylamino-1,2,4-thiadiazol-3-yl)-(Z)-2-methoxyiminoacetamido]-3-[(E)-iodo-1-propen-1-yl]-3-chepham-4-carboxylate

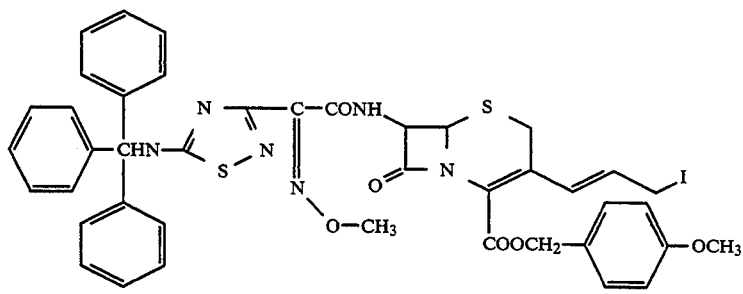

EXPERIMENT 4

Synthesis of Source Compound p-Methoxybenzyl 7β-[2-(5-tritylamino-1,2,4-thiadiazol-3-yl)-(Z)-2-methoxyiminoacetamido]-3-[(Z)-3-chloro-1-propen-1-yl]-3-cephem-4-carboxylate 7.97 G of the compound obtained in the Experiment 4 were dissolved in 167 ml of acetone, and 4.37 g of sodium iodide were added thereto. The mixture was stirred at the room temperature for one hour. The solvent was distilled off. The residue was dissolved in 150 ml of ethyl acetate, and the solution was washed with a

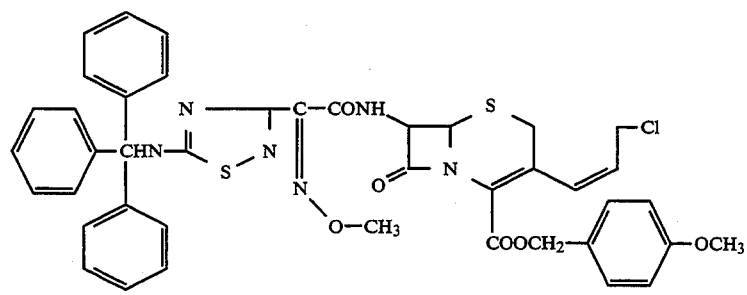

30.0 G of the compound obtained in the Experiment 3 were dissolved in a liquid mixture of 250 ml of chloroform and 300 ml of ethyl acetate, and the mixture was stirred under ice-cooling with adding 78.3 ml of an aqueous solution of 1 N sodium hydroxide. The organic layer was separated to collect, and washed with a saturated brine, followed by drying with addition of anhydrous magnesium sulfate. To this organic layer were added 6.15 g of chloroacetaldehyde solution in 10 ml of chloroform. The mixture was stirred at the room temperature for one hour. The reaction solution was concentrated, and 300 ml of ethyl acetate were added thereto. The resulting precipitate was filtered off. The filtrate was concentrated to yield 29.3 g of crude prodsaturated aqueous sodium thiosulfate solution and then a saturated brine, followed by drying with addition of anhydrous magnesium sulfate. The dried residue was concentrated under a reduced pressure. The residue was solidified by addition of n-hexane and petroleum ether and collected by filtration to yield 8.42 g of the objective compound.

EXPERIMENT 6

Synthesis of Source Compound p-Methoxybenzyl 7β-[2-(5-tritylamino-1,2,4-thiadiazol-3-yl)-(Z)-2-ethoxyiminoacetamido -3-chloromethyl-3-cephem-4-carboxylate

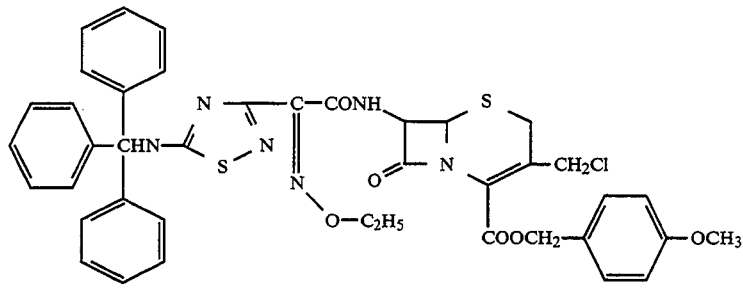

In the same manner as in the Experiment 1, 21.5 g of 2-(5-tritylamino-1,2,4-thiadiazol-3-yl)-(Z)-2-ethoxyimino acetic acid were reacted with 19.8 g of p-toluenesulfonate of p-methoxybenzyl 7β-amino-3-chloromethyl-3-cephem-4-carboxylic acid to yield 13.4 g of the objective compound.

EXPERIMENT 7

Synthesis of Source Compound p-Methoxybenzyl 7β-[2-(5-tritylamino-1,2,4-thiadiazol-3-yl)-(Z)-2-ethoxyiminoacetamido]-3-(3-chloro-1-propen-1-yl)-3-cephem-4-carboxylate

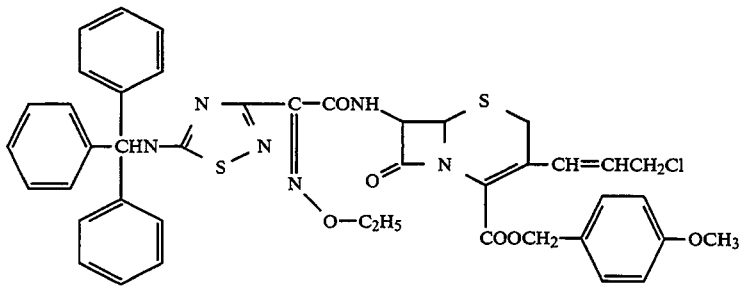

13 G of the compound obtained in the Experiment 6, 3 g of sodium iodide and 8.5 g of triphenylphosphine were suspended in 80 ml of acetone and stirred. After two hours, 300 ml of isopropyl ether were added, and 18.8 g of the resulting precipitate were collected by filtration. The precipitate was suspended in 100 ml of chloroform, and then 46 ml of 1 N aqueous solution of sodium hydroxide were added thereto. The organic layer was collected and dried with adding anhydrous magnesium sulfate thereto. Then, 3.6 g of chloroacetaldehyde were added, and the mixture was stirred for one hour. The reaction solution was concentrated under reduced pressure, and 300 ml of ethyl acetate were added thereto. The resulting precipitate was removed by filtration. The filtrate was concentrated and purified with a silica gel column chromatography to yield 3.46 g of the objective compound.

EXPERIMENT 8

Synthesis of Source Compound p-Methoxybenzyl 7β-[2-(5-tritylamino-1,2,4-thiadiazol-3-yl)-(Z)-2-ethoxyiminoacetamido-3]-(3-iodo-1-propen-1-yl)-3-cephem-4-carboxylate

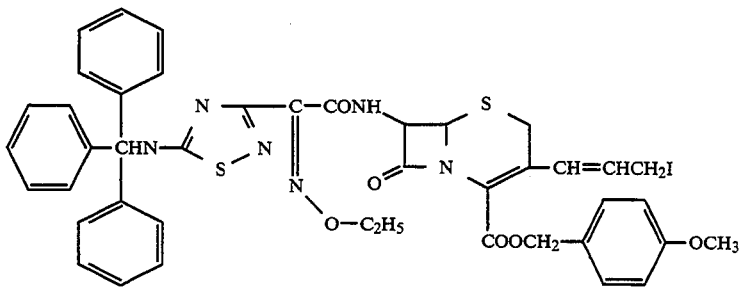

In the same manner as in the Experiment 5, 1.7 g of the compound of the Experiment 7 were reacted with 600 mg of sodium iodide to obtain 1.1 g of the objective compound.

EXPERIMENT 9

Synthesis of Source Compound

2-Ethylmethylaminoacetamide

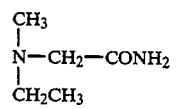

37.5 Ml of water were added to 12.5 g of ethylmethylamine and the solution was stirred under ice-cooling for one hour with further adding 20.17 g of 35% formalin and 10.98 g of sodium cyanate, followed by adding dropwise 21.1 ml of concentrated hydrochloric acid over one hour. Thereafter, the temperature was returned to the room temperature, and the whole was stirred overnight. The reaction solution was extracted with 300 ml of chloroform and the extract was dried with adding anhydrous magnesium sulfate. The solvent was distilled off to obtain light yellow oily matter.

To this matter were added 50 ml of sulfuric acid at −20° C. The temperature of the mixture was returned to the room temperature, followed by stirring for two days. The reaction solution was added to 200 ml of ice-water and neutralized with concentrated aqueous ammonia. The resulting solution was saturated with the sodium chloride, followed by extraction with 3 l of chloroform. The extract was dried with addition of anhydrous magnesium sulfate. The solvent was distilled off and the residue is recrystallized from benzene/petroleum ether to obtain 12.7 g of the objective compound in white needle crystal.

EXPERIMENT 10

Synthesis of Source Compound (R)-2-Dimethylamino-3-hydroxypropionamide

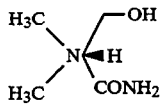

9.0 G of D-serinamide trifluoroacetate were dissolved in 12.6 ml of water. 3.47 G of sodium hydrogencarbonate were added to the solution with ice-cooling, and the solution was stirred for 10 minutes. To this solution were added 66.6 ml of acetonitrile to suspend. The suspension was cooled to −5° C. To this suspension were added 7.37 g of aqueous solution of 37% formalin and 1.74 g of sodium cyanoboronehydride, and the mixture was stirred for one hour. The insolubles deposited were removed by filtration, and the filtrate was concentrated under reduced pressure. The residue was purified by a column chromatography using 450 g of alumina to obtain 3.4 g of the objective compound.

EXPERIMENT 11

Synthesis of Source Material

1-Aza-5-methyl-4,6-dioxabicyclo [3,3,19 nonan

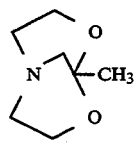

57.4 of diethanolamine were dissolved in 400 ml of tetrahydrofuran. To this solution were added 41.5 g of bromoacetone in drop-wise, and the mixture was stirred for five hours. The lower layer was removed, and the solvent in the upper layer was distilled off. To the residue was added ethyl acetate to remove oily precipitate. Thereafter, the solution was filtered by passing it through anhydrous magnesium sulfate. The solvent was distilled off from the filtrate. The residue was crystallized in a cold place, and petroleum ether was added thereto. The crystals were collected by filtration, and 34.2 g of the objective compound in coloroless prism were obtained.

EXAMPLE 1

7β-[2-(5-Amino-1,2,4-thiadiazol-3-yl)-(Z)-2-methoxyiminoacetamido]-3-[(E)-3-(carbamoylmethyldimethylammonio)-1-propen-1-yl)-3-cephem-4-carboxylate

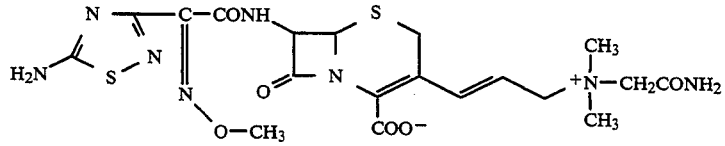

600 Mg of the compound obtained in Experiment 5 were suspended in 60 ml of ethyl ether, and then 87.3 mg of N,N-dimethylglycineamide were added thereto, followed by stirring at the room temperature for 10 minutes. To this solution, were added dropwise 43 ml of ethyl acetate over 30 minutes. After stirring the mixture for 12 hours, 20 ml of ethyl ether were added thereto, and the resulting precipitate was recovered by filtration. The precipitate was dissolved in 1 ml of tetrahydrofuran, and then 10 ml of ethyl acetate were added to the solution. The resulting precipitate was recovered by filtration to yield 279 mg of a yellow powder.

This product was added to a liquid mixture of 3.32 ml of trifluoroacetic acid and 1.75 ml anisole, followed by stirring under ice-cooling for 3 hours. The reaction solution was added to 50 ml of ethyl ether and 50 ml of isopropyl ether. The resulting precipitate was recovered by filtration and washed with ethyl ether. The precipitate was added to 1.8 ml of water, and pH of the solution was adjusted to 6.0 by means of sodium acetate. Insoluble matters are removed by filtration. The filtrate was purified by a reverse-phase silica gel column chromatography to yield 51 mg of the objective compound.

EXAMPLE 2

7β-[2-(5-Amino-1,2,4-thiadiazol-3-yl)-(Z)-2-methoxyiminoacetamido]-3-[(E)-3-(1-methyl-3-pyrrolinio)-1-propene-1-yl)-3-cephem-4-carboxylate

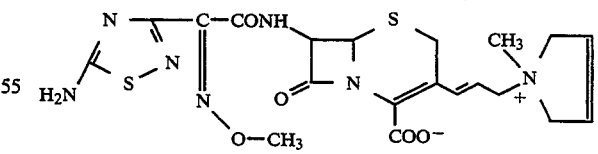

500 Mg of the compound obtained in Experiment 5 were suspended in 50 ml of ethyl ether and then a solution of 59.2 mg of N-methyl-3-pyrroline in 5 ml of ethyl acetate was added thereto, followed by stirring at the room temperature for one hour. To this solution, 32 ml of ethyl acetate were added dropwise over 3 hours and 30 minutes. After 4 hours, 20 ml of ethyl ether were added and the mixture was stirred for 13 hours. The resulting precipitate was recovered by filtration and dissolved in 0.88 ml of tetrahydrofuran. To this solution, 9 ml of ethyl acetate were added and the resulting precipitate was recovered by filtration to yield 283 mg of a yellow powder.

This yellow powder was added to a liquid mixture of 3.3 ml of trifluoroacetic acid and 1.8 ml of anisole, followed by stirring under ice-cooling for 3 hours. The reaction solution was added to a liquid mixture of 50 ml of ethyl ether and 50 ml of isopropyl ether, and the resulting precipitate was recovered by filtration. To this precipitate, 1.8 ml of water were added and the pH of the solution was adjusted to 6.8 with sodium acetate, followed by the removal of insoluble matters by filtration. The filtrate was purified by a reversed-phase silica gel column chromatography (elution: 5.5% aqueous methanol, 6.5% aqueous methanol) to yield 47 mg of the objective compound.

EXAMPLE 3

7β-[2-(5-Amino-1,2,4-thiadiazol-3-yl)-(Z)-2-methoxyiminoacetamido]-3-[(E)-3-((2S)-2-hydroxymethyl-1-methylpyrrolidinio)-1-propen-1-yl]-3-cephem-4-carboxylate

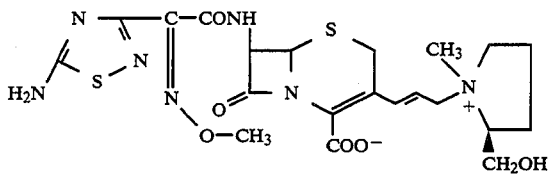

900 Mg of the compound obtained in Experiment 5 were suspended in 90 ml ethyl ether and then a solution of 147.6 mg of N-methyl-L-prolinol in 9 ml of ethyl acetate were added thereto at the room temperature. After 10 minutes, 57.6 ml of ethyl acetate were added dropwise over 2 hours. After stirring this solution for 1 hour, a solution of 73.8 mg of N-methyl-L-prolinol in 3 ml of ethyl ether was added and continued the stirring for additional 14 hours. 10 Ml of ethyl ether were added to the solution and the resulting precipitate was recovered by filtration. This precipitate was dissolved in 1.3 ml of tetrahydrofuran, and then 13 ml of ethyl acetate were added thereto. The resulting precipitate was recovered by filtration to yield 546 mg of a yellow powder.

This yellow powder was added to a liquid mixture of 3.9 ml of trifluoroacetic acid and 3.3 ml of anisole, followed by stirring under ice-cooling for 2 hours. The reaction solution was added to a liquid mixture of 90 ml of ethyl ether and 90 ml of isopropylether, and the resulting precipitate was recovered by filtration. To this precipitate, 1.8 ml of water were added. The pH of the solution was adjusted to 5.7 with sodium acetate, followed by removal of insoluble matters by filtration. The filtrate was purified by reversed-phase silica gel column chromatography (elution: 5.5% aqueous methanol, 6.5% aqueous methanol and 7.5% aqueous methanol) to yield 19 61 mg of the objective compound.

EXAMPLE 4

7β-[2-(5-Amino-1,2,4-thiadiazol-3-yl)-(Z)-2-methoxyiminoacetamido]-3-[(E)-3-(4-carbamoylquinuclidinio)-1-propen-1-yl]-3-cephem-4-carboxylate

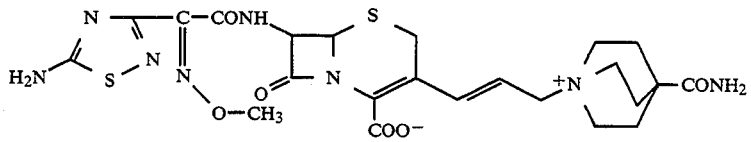

500 Mg of the compound obtained in Experiment 5 were suspended in 50 ml of ethyl ether, and then 110 mg of 4-carbamoylquinuclidine were added thereto, and the whole was stirred at the room temperature for one hour and 30 minutes. 50 Ml of ethyl acetate were added dropwise over 2 hours, and the stirring was continued for additional 22 hours. The resulting precipitate was recovered by filtration. This precipitate was dissolved in 0.9 ml of tetrahydrofuran, and then 9 ml of ethyl acetate were added thereto. The resulting precipitate was recovered by filtration to yield 318 mg of a yellow powder.

This yellow powder was added to a liquid mixture of 2.3 ml of trifluoroacetic acid and 2.8 ml of anisole, followed by stirring at the room temperature for 2 hours and 30 minutes. The reaction solution was added to 100 ml of ethyl ether and the resulting precipitate was recovered by filtration. This precipitate was suspended in 1.8 ml of water. After adjusting the pH of the solution to 5.3 with sodium hydrogen carbonate, insoluble matters were removed by filtration. The filtrate was purified by a reversed-phase silica gel chromatography (elution: 5% aqueous methanol) to yield 50 mg of the objective compound.

EXAMPLE 5

7β-[(2-(5-Amino-1,2,4-thiadiazol-3-yl)-(Z)-2-methoxyiminoacetamido]-3-[(E)-3-(1-methyl-1-piperadinio)-1-propen-1-yl]-3-cephem-4-carboxylate trifluoroacetate

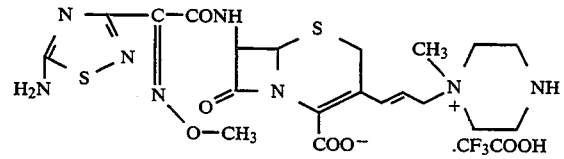

984 Mg of the compound obtained in Experiment 5 were suspended in 98 ml of ethyl ester, and then 115 μl of 1-methylpiperazine were added thereto, followed by stirring at the room temperature for 1 hour. Thereafter, 94 ml of ethyl acetate were added dropwise over 2 hours. After stirring for 20 hours, the resulting precipitate was recovered by filtration. This precipitate was dissolved in 1.6 ml of tetrahydrofuran, and then 16 ml of ethyl acetate were added thereto to reprecipitate. This operation was repeated twice to yield 411 mg of a yellow powder.

The yellow powder was added to a liquid mixture of 2.9 ml of trifluoroacetic acid and 2.5 ml of anisole, followed by stirring at the room temperature for 30 minutes. The reaction solution was added to a liquid mixture of 50 ml of ethyl ether and 50 ml of isopropyl ether. The resulting precipitate was recovered by filtration.

To this precipitate, 3 ml of water were added and insoluble matters were removed by filtration. The filtrate was purified by a reversed-phase silica gel column chromatography (elution: 5.5% aqueous methanol, 7.5% aqueous methanol) to yield 19 mg of the objective compound.

The following compounds in Examples 6–17 were synthesized in the same manner as Examples 1–5.

EXAMPLE 6

7β-[2-(5-Amino-1,2,4-thiadiazol-3-yl)-(Z)-2-methoxyacetamido]-3-[(E)-3-(4-carboxyquinuclidinio)-1-propene-1-yl]-3-cephem-4-carboxylate 800 Mg of the compound obtained in Experiment 5 were reacted with 176.8 mg of 4-carboxyquinuclidine to yield 15 mg of the objective compound.

EXAMPLE 7

7β-[2-(5-Amino-1,2,4-thiadiazol-3-yl)-(Z)-2-methoxyiminoacetamido]-3-[(E)-3-[(2S)-2-carboxy-1-methylpyrrolidinio]-1-propen-1-yl]-3-cephem-4-carboxylate

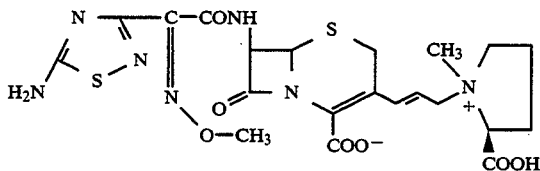

800 Mg of the compound obtained in Experiment 5 were reacted with 317 mg of N-methyl-L-proline to yield two isomers (relating to steric configuration of methyl group bonding to the nitrogen atom on the pyrrolidine ring) as the objective compound.

| Isomer A | 12 mg |
| Isomer B | 20 mg |

EXAMPLE 8

7β-[2-(5-Amino-1,2,4-thiadiazol-3-yl)-(Z)-2-methoxyiminoacetamido]-3-[(E)-3-carboxymethyldimethylammonio)-1-propen-1-yl]-3-cephem-4-carboxylate

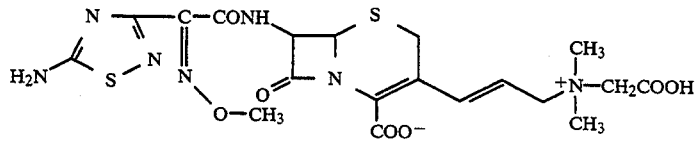

800 Mg of the compound obtained in Experiment 5 were reacted with 117.5 mg of N,N-dimethylglycine to yield 12 mg of the objective compound.

EXAMPLE 9

7β-[2-(5-Amino-1,2,4-thiadiazol-3-yl)-(Z)-2-methoxyiminoacetamido]-3-[(E)-3-(3-carboxypyridinio)-1-propen-1-yl]-3-cephem-4-carboxylate

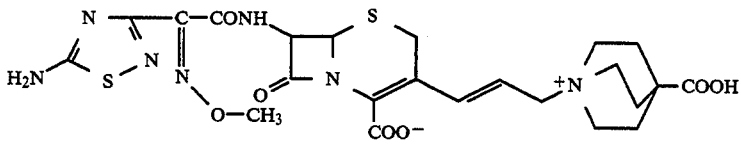

1.0 G of the compound obtained in Experiment 5 were reacted with 405 mg of nicotinic acid to yield 35 mg of the objective compound.

EXAMPLE 10

7β-[2-(5-Amino-1,2,4-thiadiazol-3-yl)-(Z)-2-methoxyiminoacetamido]-3-[(E)-3-(1,5-tetramethylene-2-pyrazolio)-1-propen-1-yl]-3-cephem-4-carboxylate

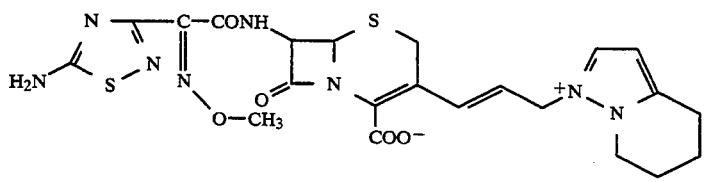

600 Mg of the compound obtained in Experiment 5 were reacted with 0.6 ml of 1,5-tetramethylenepyrazole to yield 11 mg of the objective compound.

EXAMPLE 11

7β-[2-(5-Amino-1,2,4-thiadiazol-3-yl)-(Z)-2-methoxyiminoacetamido]-3-[(E)-3-(carbamoylmethyldiethylammonio)-1-propen-1-yl]-3-cephem-4-carboxylate

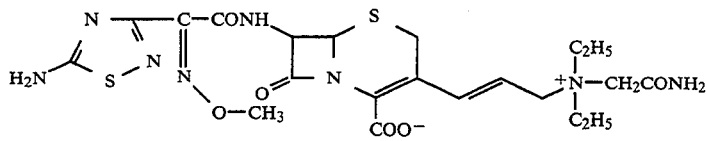

500 Mg of the compound obtained in Experiment 5 were reacted with 93 mg of N,N-diethylglycineamide to yield 6 mg of the objective compound.

EXAMPLE 12

7β-[2-(5-Amino-1,2,4-thiadiazol-3-yl)-(Z)-2-methoxyiminoacetamido]-3-[(E)-3-(2-dimethylaminoethyldimethylammonio)-1-propen-1-yl]-3-cephem-4-carboxylate

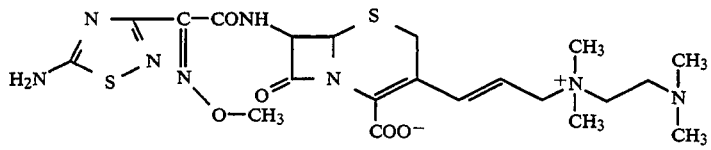

800 Mg of the compound obtained in Experiment 5 were reacted with 172 μl of 1,2-bis(dimethylamino)ethane to yield 14 mg of the objective compound.

EXAMPLE 13

7β-[2-(5-Amino-1,2,4-thiadiazol-3-yl)-(Z)-2-methoxyiminoacetamido]-3-[(E)-(2-mercaptoethyldimethylammonio)-1-propen-1-yl]-3-cephem-4-carboxylate

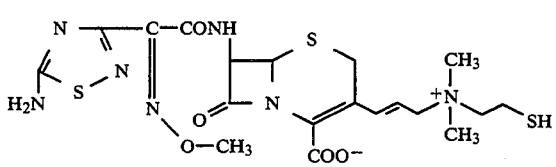

500 Mg of the compound obtained in Experiment 5 were reacted with 200 mg of 2-dimethylaminoethanethiol to yield 2.5 mg of the objective compound.

EXAMPLE 14

7β-[2-(5-Amino-1,2,4-thiadiazol-3-yl)-(Z)-2-methoxyiminoacetamido]-3-[(E)-(1-morpholino[4,3-b]pyrazolio)-1-propen-1-yl]-3-cephem-4-carboxylate

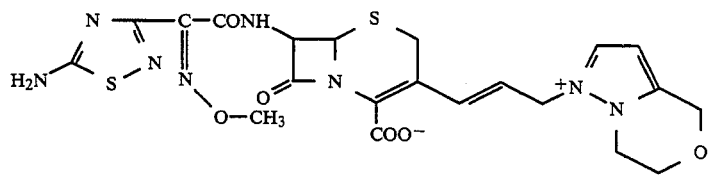

1.0 G of the compound obtained in Experiment 5 were reacted with 408 mg of morpholino[4,3-b]pyrazole to yield 11 mg of the objective compound.

EXAMPLE 15

7β-[2-(5-Amino-1,2,4-thiadiazol-3-yl)-(Z)-2-ethoxyiminoacetamido]-3-[(E)-3-(carbamoylmethyldimethylammonio)-1-propen-1-yl]-3-cephem-4-carboxylate

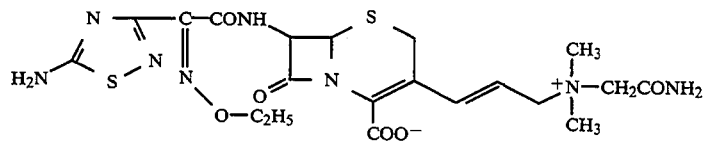

1.0 G of the compound obtained in Experiment 8 were reacted with 230 mg of N,N-dimethylglycineamide to yield the objective compound.

EXAMPLE 16

7β-[2-(5-Amino-1,2,4-thiadiazol-3-yl)-(Z)-2-methoxyiminoacetamido]-3-[(E)-3-[4-(methylthio)quinuclidinio]-1-propen-1-yl]-3-cephem-4-carboxylate

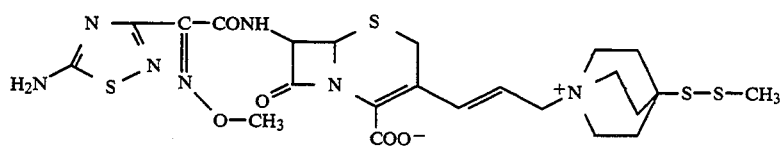

500 Mg of the compound obtained in Experiment 5 were reacted with 350 mg of 4-(methyldithio)quinuclidine to yield 28 mg of the objective compound.

EXAMPLE 17

7β-[2-(5-Amino-1,2,4-thiadiazol-3-yl)-(Z)-2-methoxyiminoacetamido]-3-[(E)-3-(2-oxopropyldimethylammonio)-1-propen-1-yl]-3-cephem-4-carboxylate

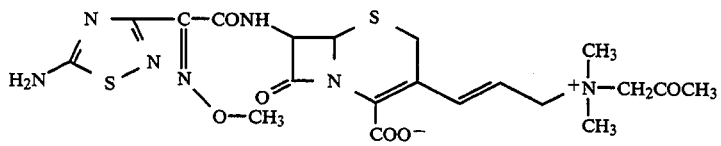

500 Mg of the compound obtained in Experiment 5 were reacted with 100 mg of N,N-dimethylaminoacetone to yield 36 mg of the objective compound.

EXAMPLE 18

7β-[2-(5-Amino-1,2,4-thiadiazol-3-yl)-(Z)-2-methoxyiminoacetamido]-3-[(E)-3-(2-hydroxyethyldimethylammonio)-1-propen-1-yl]-3-cephem-4-carboxylate (Compound A)

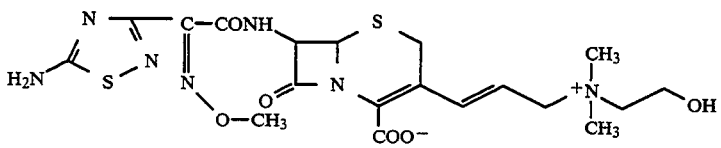

7β-[2-(5-Amino-1,2,4-thiadiazol-3-yl)-(Z)-2-methoxyiminoacetamido -3-[(Z)-3-(2-hydroxyethyldimethylammonio)-1-propen-1-yl]-3-cephem-4-carboxylate (Compound B)

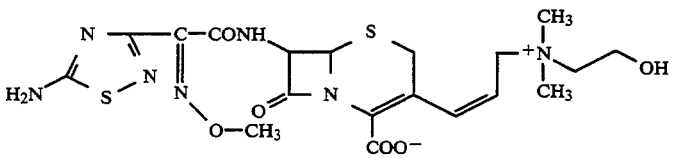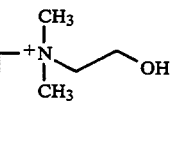

500 Mg of the compound obtained in Experiment 4, 142 mg of sodium iodide and 10 ml of 2-butanone were stirred at room temperature for one hour. The solvent was distilled off. The residue was dissolved in ethyl acetate. The resulting solution was washed with 10% aqueous solution of sodium thiosulfate and saturated brine, followed by drying with an addition of anhydrous magnesium sulfate. The solvent was distilled off, and the residue was dissolved in a liquid mixture of 30 ml of ethyl acetate and 10 ml of ethyl ether. To this solution were added 112 mg of N,N-dimethylaminoethanol, and the solution was stirred at the room temperature for one hour and 30 minutes. 20 Ml of ethyl ether were added to the solution. The resulting precipitate was recovered by filtration. This precipitate was washed with isopropyl ether to yield 370 mg of a yellow powder.

This yellow powder was added, under ice-cooling, to a liquid mixture of 0.8 ml of anisole and 8 ml of trifluoroacetic acid, and the whole was stirred at the same temperature for one hour. To the reaction solution were added 20 ml of isopropyl ether, and the resulting precipitate was recovered by filtration. To this precipitate was added 30% aqueous methanol. Insoluble matters were removed by filtration. The pH of the filtrate was adjusted to 5 by an addition of sodium acetate. The solvent was distilled off. The residue was purified by a reversed-phase silica gel column chromatography (elution: 5% aqueous methanol) to yield 25 mg of the objective compound A and 17 mg of the compound B.

EXAMPLE 19

7β-[2-(5-Amino-1,2,4-thiadiazol-3-yl)-(Z)-2-methoxyiminoacetamido -3-[(Z)-3-(carbamoylmethyldimethylammonio)-1-propen-1-yl]-3-cephem-4-carboxylate

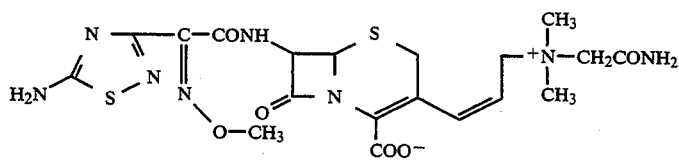

1.031 G of the compound obtained in Experiment 3 were dissolved in a liquid mixture of 20 ml of ethyl acetate and 6 ml of chloroform, and then 20 ml of 10% aqueous solution of potassium carbonate were added thereto, followed by shaking. The organic layer was taken out and dried with an addition of anhydrous potassium carbonate, followed by washing with 6 ml of ethyl acetate. A solution of 85 ml of chloroacetaldehyde in 0.25 ml of ethyl acetate was added thereto under ice-cooling, followed by stirring for 4 hours. Thereafter, 137 mg of N,N-dimethylglycinamide and a solution of 50 mg of sodium iodide in 1 ml of acetone were added thereto, followed by stirring at the room temperature overnight. The deposits were recovered by filtration and dried. The deposits were dissolved in 1.4 ml of anisole and the resulting solution was stirred for one hour under ice-cooling with an addition of 1.9 ml of trifluoroacetic acid. To the reaction solution were added 100 ml of a liquid mixture of isopropyl ether - ethyl ether (1:1), and the resulting precipitates were recovered by filtration. The precipitates were washed with ethyl ether, and dried to obtain 20 mg of solid. This solid was dissolved in a liquid mixture of 1.5 ml of water - 1.0 ml of an aqueous saturated solution of acetate, and the insoluble matters were removed by filtration. The filtrate was purified by a reversed-phase silica gel column chromatography (elution: a gradient of water-6% aqueous methanol) to yield 5 mg of the objective compound.

EXAMPLE 20

7β-[2-(5-Amino-1,2,4-thiadiazol-3-yl)-(Z)-2-methoxyiminoacetamido]-3-[(E)-3-[(1,3,4-oxadiazol-2-yl)methyldimethylammonio]-1-propen-1-yl]-3-cephem-4-carboxylate

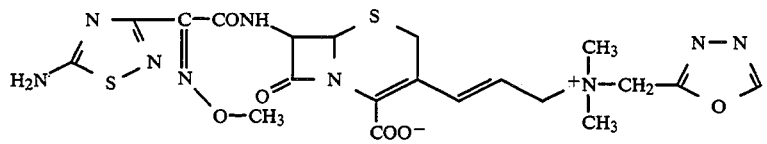

500 Mg of the compound obtained in Experiment 5 were suspended in 10 ml of ethyl ether, followed by adding 120 mg of 2-dimethylaminomethyl-1,3,4-oxadiazol. The mixture was stirred at the room temperature for one hour. To this reaction solution were added 50 ml of ethyl ether. The resulting precipitate was recovered by filtration to yield 510 mg of a yellow powder.

This yellow powder was added to a liquid mixture of 2.5 ml of trifluoroacetic acid and 2.5 ml of anisole, followed by stirring under ice-cooling for 3 hours. To this reaction solution, 50 ml of isopropyl ether were added, and the resulting precipitate was recovered by filtration. This precipitate was suspended in 20 ml of water. The pH of the suspension was adjusted to 7–8 by an addition of sodium hydrogencarbonate. The insoluble matters were removed by filtration. The filtrate was purified by a reversed-phase silica gel chromatography to yield 13 mg of the objective compound.

EXAMPLE 21

7β-[2-(5-Amino-1,2,4-thiadiazol-3-yl)-(Z)-2-methoxyiminoacetamido -3-[(E)-3-[(1,2,4-oxadiazol-3-yl)methyldimethylammonio]-1-propen-1-yl]-3-cephem-4-carboxylate

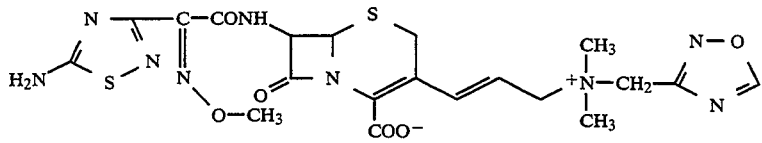

500 Mg of the compound obtained in Experiment 5 were suspended in 10 ml of ethyl ether, and then 120 mg of 3-dimethylaminomethyl-1,2,4-oxadiazol were added thereto, followed by stirring at the room temperature for one hour. To this reaction solution were added 50 ml of ethyl ether. The resulting precipitate was recovered by filtration to yield 480 mg of a yellow powder.

This yellow powder was added to a liquid mixture of 2.5 ml of trifluoroacetic acid and 2.5 ml of anisole, followed by stirring under ice-cooling for 3 hours. To this reaction solution were added 50 ml of isopropyl ether, and the resulting precipitate was recovered by filtration. This precipitate was suspended in 2 ml of water. The pH of the suspension was adjusted to 7–8 by an addition of sodium hydrogencarbonate. The insoluble matters were removed by filtration. The filtrate was purified by a reversed-phase silica gel chromatography to yield 34 mg of the objective compound.

EXAMPLE 22

7β-[2-(5-Amino-1,2,4-thiadiazol-3-yl)-(Z)-2-methoxyiminoacetamido -3-[(E)-3-[(imidazol-4-yl)-methyldimethylammonio]-1-propen-1-yl]-3-cephem-4-carboxylate

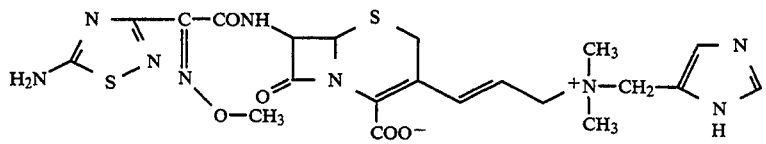

500 Mg of the compound obtained in Experiment 5 were suspended in 10 ml of ethyl ether, and then 125 mg of 4-(dimethylaminomethyl)imidazole were added thereto, followed by stirring for one hour. To this reaction solution were added 50 ml of ethyl ether. The resulting precipitate was recovered by filtration to yield 382 mg of a yellow powder.

This yellow powder was added to a liquid mixture of 2.5 ml of trifluoroacetic acid and 2.5 ml of anisole, followed by stirring under ice-cooling for 3 hours. To this reaction solution were added 50 ml of isopropyl ether, and the resulting precipitate was recovered by filtration. This precipitate was suspended in 2 ml of water. The pH of the suspension was adjusted to 7–8 by an addition of sodium hydrogencarbonate. The insoluble matters were removed by filtration. The filtrate was purified by a reversed-phase silica gel chromatography to yield 23 mg of the objective compound.

Compounds in the following Examples 23–26 were prepared in the same manner as described in Examples 20–22.

EXAMPLE 23

7β-[2-(5-Amino-1,2,4-thiadiazol-3-yl)-(Z)-2-methoxyiminoacetamido]-3-[(E)-3[(thiazol-4-yl)methyldimethylammonio]-1-propen-1-yl]-3-cephem-4-carboxylate

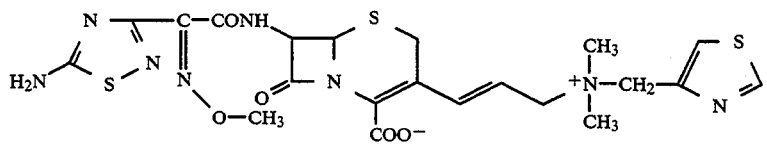

500 Mg of the compound obtained in the Experiment 5 were reacted with 126 mg of 4-dimethylaminomethyl thiazol, followed by removing the protective group to yield 33 mg of the objective compound.

EXAMPLE 24

7β-[2-(5-Amino-1,2,4-thiadiazol-3-yl)-(Z)-2-methoxyiminoacetamido]-3-[(E)-3-[(pyrazol-3-yl)methyldimethylammonio]-1-propen-1-yl]-3-cephem-4-carboxylate

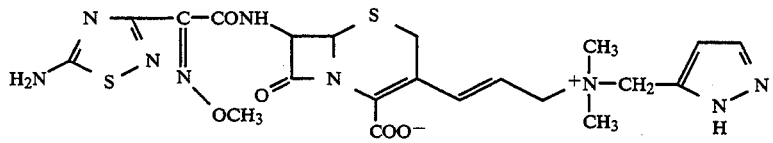

500 Mg of the compound obtained in the Experiment 5 were reacted with 120 mg of 3-dimethylaminomethyl pyrazole, followed by removing the protective group to yield 200 mg of the objective compound.

EXAMPLE 25

7β-[2-(5-Amino-1,2,4-thiadiazol-3-yl)-(Z)-2-methoxyiminoacetamido]-3-[(E)-3-(2-aminothiazol-4-yl)-methyldimethylammonio]-1-propen-1-yl]-3-cephem-4-carboxylate

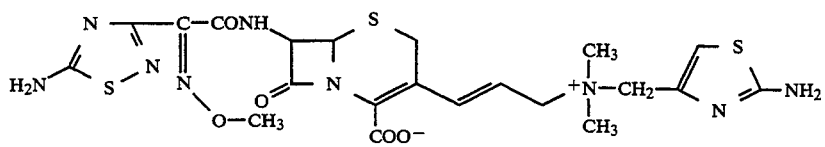

500 Mg of the compound obtained in the Experiment 5 were reacted with 140 mg of 2-amino-4-dimethylaminomethylthiazole, followed by removing the protective group to yield 58 mg of the objective compound.

EXAMPLE 26

7β-[2-(5-Amino-1,2,4-thiadiazol-3-yl)-(Z)-2-methoxyiminoacetamido]-3-[(E)-3-[(furan-3-yl)-methyldimethylammonio]-1-propen-1-yl]-3-cephem-4-carboxylate

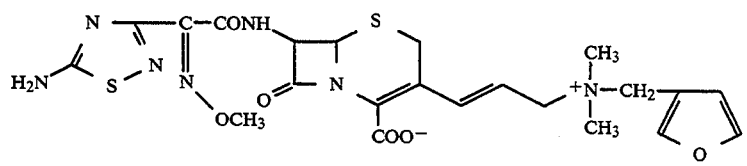

500 Mg of the compound obtained in the Experiment 5 were reacted with 125 mg of 3-dimethylaminomethyl furan, followed by removing the protective group to yield 35 mg of the objective compound.

EXAMPLE 27

7β-[2-(5-Amino-1,2,4-thiadiazol-3-yl)-(Z)-2-methoxyiminoacetamido]-3-[(E)-3-(1-methyl-4-sulfamoyl-1-piperazinio)-1-propen-1-yl]-3-cephem-4-carboxylate

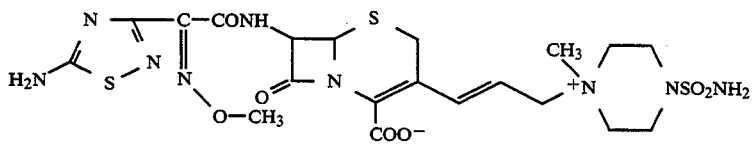

1.0 G of the compound obtained in the Experiment 5 was dissolved in 5 ml of dichloromethane, to which solution 255 mg of N-sulfamoyl-N'-methylpiperazine were added under ice-cooling. The whole was stirred overnight at a room temperature. To the reaction solution were added 10 ml of ethyl acetate and 10 ml of ethyl ether. The resulting precipitate was collected by filtration. The precipitate was dissolved in a small amount of a mixed solution of methanol/tetrahydrofuran. To the solution were added 40 ml of ethyl acetate. The resulting precipitate was collected by filtration to yield 731 mg of yellow powder.

The above compound was added to a mixed solution of 5.2 ml of trifluoroacetic acid and 4.4 ml of anisole, and the mixture was stirred under ice-cooling for 2 hours. The reaction solution was introduced in a mixed solution of 50 ml of ethyl ether and 50 ml of isopropyl ether. The formed precipitate was collected by filtration, followed by washing with ethyl ether. To the resulting precipitate was added 1 ml of water, and then adjusted to pH of 5.5 with sodium acetate. The insoluble matter was filtered off. The filtrate was purified by a reverse phase silica gel column chromatography to yield 30 mg of the objective compound.

EXAMPLE 28

7β-[2-(5-Amino-1,2,4-thiadiazol-3-yl)-(Z)-2-methox- yiminoacetamido]-3-[(E)-3-(1-methyl-4-formimidoyl-1- piperazinio)-1-propen-1-yl]-3-cephem-4-carboxylate

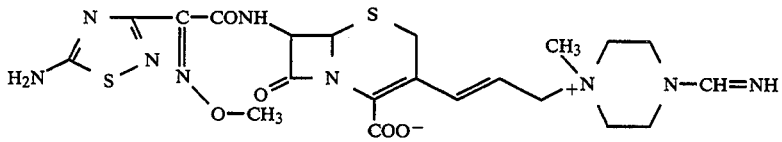

1.5 G of the compound obtained in the Experiment 5 were dissolved in a mixed solution of 10 ml of methanol and 4 ml of dimethyl formamide. To the solution were added 323 mg of N-methyl-N'-formimidoyl piperazine hydrochloride, and the whole was stirred overnight. The reaction solution was added in 200 ml of ethyl acetate, and the formed precipitate (594 mg) was collected by filtration.

The precipitate was added to a mixed solution of 4.2 ml of trifluoro-acetic acid and 3.6 ml of anisole, and the whole was stirred for 2 hours under ice-cooling. The reaction solution was added to the mixed solution of 50 ml of ethyl ether and 50 ml of isopropyl ether, and the formed precipitate was collected by filtration. To the precipitate was added 1 ml of water, and the insoluble matter was filtered off. The filtrate was purified by a reverse phase silica gel column chromatography to yield 20 mg of the objective compound.

EXAMPLE 29

7β-[2-(5-Amino-1,2,4-thiadiazol-3-yl)-(Z)-2-methox- yiminoacetamido]-3-[(E)-3-(1-methyl-4-carbamoyl-1- piperazinio)-1-propen-1-yl]-3-cephem-4-carboxylate

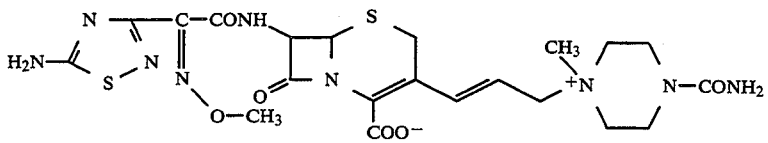

1.0 G of the compound obtained in the Experiment 5 were dissolved in 50 ml of ethyl acetate. To the solution were added 204 mg of N-methyl-N'-carbamoyl piperazine, and the whole was stirred overnight at a room temperature. The formed precipitate was collected by filtration to yield 867 mg of yellow powder.

The above compound was added to a mixed solution of 6.2 ml of trifluoro-acetic acid and 5.3 ml of anisole, and the whole was stirred for 2 hours under ice-cooling. The precipitate was collected by filtration, 1 ml of water was added to the precipitate, and the whole was adjusted to pH of 5 with sodium acetate. The insoluble matter was filtered off, and the filtrate was purified by a reverse phase silica gel column chromatography to yield 40 mg of the objective compound.

EXAMPLE 30

7β-[2-(5-Amino-1,2,4-thiadiazol-3-yl)-(Z)-2-methox- yiminoacetamido]-3-[(E)-(1,2-dimethyl-1-pirazolydini- o)-1-propen-1-yl]-3-cephem-4-carboxylate

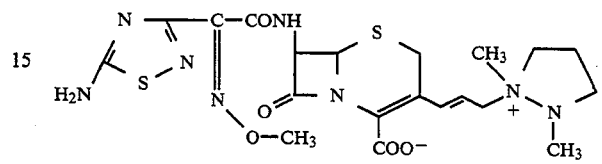

1.0 G of the compound obtained in the Experiment 5 were suspended in 150 ml of ethyl ether; and 143 mg of N,N'-dimethylpiperazolydine were added to the suspension; and the whole was stirred overnight at the room temperature. The formed precipitate was collected by filtration, and the precipitate was dissolved in 1.5 ml of tetrahydrofuran. To the solution was added 20 ml of ethyl acetate, and the formed precipitate was collected by filtration to yield 491 mg of yellow powder.

The above compound was added to a mixed solution of 3.5 ml of trifluoro-acetic acid and 3.0 ml of anisole, and the whole was stirred for 2 hours under ice-cooling. The reaction solution was added to a mixed solution of 50 ml of ethyl ether and 50 ml of isopropyl ether, and the formed precipitate was collected by filtration. To the precipitate was added 1 ml of water, and the whole was adjusted to pH of 6.0 with sodium acetate. The insoluble matter was filtered off, and the filtrate was purified by a reverse phase silica gel column chromatography to yield 19 mg of the objective compound (total of two stereoisomers A and B; A:8 mg, and B:11 mg).

EXAMPLE 31

7β-[2-(5-Amino-1,2,4-thiadiazol-3-yl)-(Z)-2-methox- yiminoacetamido]-3-[(E)-3-(1,1-dioxo-4-methyl-4-thi- omorpholinio)-1-propen-1-yl]-3-cephem-4-carboxylate

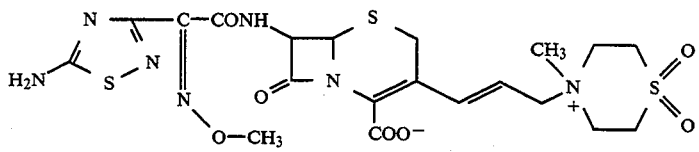

1.0 G of the compound obtained in the Experiment 5 was dissolved in 3 ml of dichloromethane. To the solution were added 327 mg of 4-methyl thiomorpholine 1,1-dioxide, and the whole was stirred overnight at a room temperature. To the reaction solution were added 10 ml of ethyl acetate to collect the formed precipitate (783 mg) by filtration.

The above compound was added to a mixed solution of 5.6 ml of trifluoro-acetic acid and 4.8 ml of anisole, and the whole was stirred for 2 hours under ice-cooling. The reaction solution was added in 100 ml of ethyl ether, and the formed precipitate was collected by filtration. To the precipitate was added 1 ml of water, and the whole was adjusted to pH of 7.0 with sodium acetate. The insoluble matter was filtered off, and the filtrate was purified by a reverse silica gel column chromatography to yield 29 mg of the objective compound.

EXAMPLE 32

7β-[2-(5-Amino-1,2,4-thiadiazol-3-yl)-(Z)-2-methoxyiminoacetamido]-3-[(E)-3-(1,4-diazabicyclo[2,2,2]octan-1-io)-1-propen-1-yl]-3-cephem-4-carboxylate

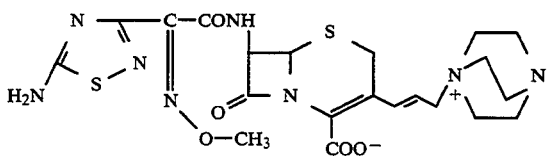

1.0 G of the compound obtained in the Experiment 5 was dissolved in 150 ml of ethyl ether, to which solution 148 mg of 1,4-diazabicyclo[2,2,2]octane were added. The whole was stirred overnight at a room temperature. The formed precipitate was collected by filtration, and the precipitate was dissolved in 2 ml of tetrahydrofuran. The solution was added in 20 ml of ethyl acetate, and the formed precipitate was collected by filtration to obtain 746 mg of yellow powder.

The above compound was added to a mixed solution of 5.3 ml of trifluoro-acetic acid and 3.4 ml of anisole, and the whole was stirred for 2 hours under ice-cooling. The reaction solution was added in 100 ml of ethyl ether, and the formed precipitate was collected by filtration. To the precipitate were added 1.8 ml of water, and the insoluble matter was filtered off. The filtrate was purified by a reverse phase silica gel column chromatography to yield 83 mg of the objective compound.

In the same manner as in the Examples 27–32, there were produced the compounds of the following Examples 33–38.

EXAMPLE 33

7β-[2-(5-Amino-1,2,4-thiadiazol-3-yl)-(Z)-2-methoxyiminoacetamido]-3-[(E)-3-(1,4-dimethyl-1-piperazinio)-1-propen-1-yl]-3-cephem-4-carboxylate

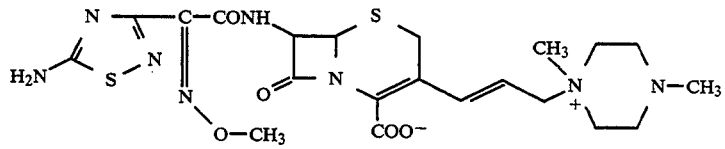

1.0 G of the compound obtained in the Experiment 5 was reacted with 193 μl of 1,4-dimethylpiperazine, and the protective group was removed to yield 15 mg of the objective compound.

EXAMPLE 34

7β-[2-(5-Amino-1,2,4-thiadiazol-3-yl)-(Z)-2-methoxyiminoacetamido]-3-[(E)-3-(1-methyl-4-carbamoyl-1,2,3,6-tetrahydropyridinio)-1-propen-1-yl]-3-cephem-4-carboxylate

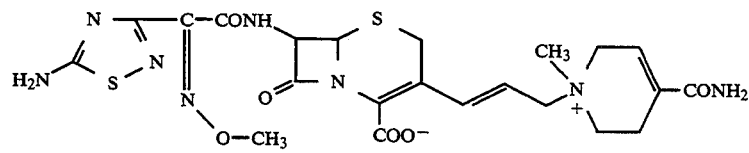

600 Mg of the compound obtained in the Experiment 5 were reacted with 137 mg of 1-methyl-carbamoyl-1,2,3,6-tetrahydropyridine, and the protective group was removed to yield 45 mg of the objective compound.

EXAMPLE 35

7β-[2-(5-Amino-1,2,4-thiadiazol-3-yl)-(Z)-2-methoxyiminoacetamido]-3-[(E)-3-[N,N-dimethyl-N-(2-carbamoylethyl)ammonio]-1-propen-1-yl]-3-cephem-4-carboxylate

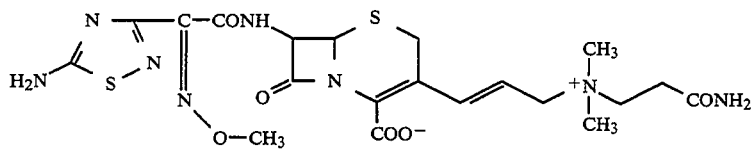

500 Mg of the compound obtained in the Experiment 5 were reacted with 127 mg of 3-dimethylaminopropionamide, and the protective group was removed to yield 12 mg of the objective compound.

EXAMPLE 36

7β-[2-(5-Amino-1,2,4-thiadiazol-3-yl)-(Z)-2-methoxyiminoacetamido]-3-[(E)-3-(1,1-dimethyl-1-hydrazinio)-1-propen-1-yl]-3-cephem-4-carboxylate

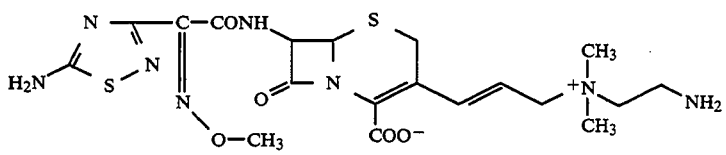

600 Mg of the compound obtained in the Experiment 5 were reacted with 60 mg of 1,1-dimethyl-1-hydrazine, and the protective group was removed to yield 50 mg of the objective compound.

EXAMPLE 37

7β-[2-(5-Amino-1,2,4-thiadiazol-3-yl)-(Z)-2-methoxyiminoacetamido]-3-[(E)-3-(N,N-dimethyl-N-hydrazinocarbonylmethylammonio)-1-propen-1-yl]-3-cephem-4-carboxylate

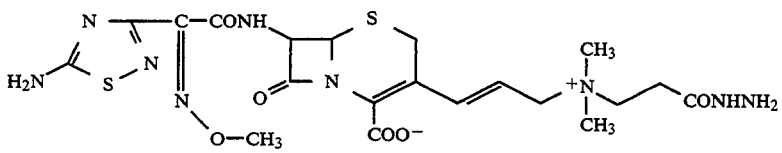

500 Mg of the compound obtained in the Experiment 5 were reacted with 110 mg of N,N-dimethylacetohydrazine, and the protective group was removed to yield 14 mg of the objective compound.

EXAMPLE 38

7β-[2-(5-Amino-1,2,4-thiadiazol-3-yl)-(Z)-2-methoxyiminoacetamido]-3-[(E)-3-(1,5-diazabicyclo[3,3,0]octan-1-io)-1-propen-1-yl]-3-cephem-4-carboxylate

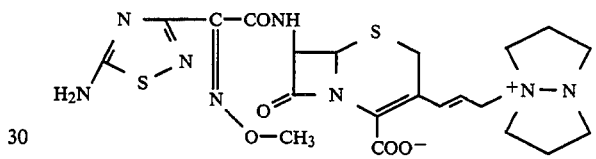

750 Mg of the compound obtained in the Experiment 5 were reacted with 280 mg of 1,5-diazabicyclo[3,3,0]octane, and the protective group was removed to yield 35 mg of the objective compound.

TABLE 1

(List of physical value)

| Experiment No. | Infra-red Absorption Spectrum (cm$^{-1}$, Nujol) | NMR (δ) |
|---|---|---|
| 1 | 1765, 1715, 1680, 1600, 1575 | (DMSO-d$_6$) 3.5–3.7(2H, br), 3.74(3H, s), 3.98(3H, s), 4.46(2H, s), 5.15(1H, d, J=5Hz), 5.19(2H, s), 5.89(1H, dd, J=5Hz, 8Hz) 6.90(2H, d, J=9Hz), 7.29(15H, s), 7.34(2H, d, J=9Hz), 9.52(1H, d, J=8Hz), 9.97(2H, s) |
| 2 | 1765, 1715, 1670, 1600, 1580 | (CDCl$_3$) 3.42(1H, d, J=18Hz), 3.70(1H, d, J=18Hz), 3.76(3H, s), 4.08(3H, s), 4.23(1H, d, J=9Hz), 4.38(1H, d, J=9Hz), 4.94(1H, d, J=5Hz), 5.16(2H, s), 5.82(1H, dd, J=5Hz, 9Hz), 6.79(1H, d, J=9Hz), 6.80(2H, d, J=9Hz), 7.22(15H, m), 7.27(2H, d, J=9Hz), 7.55(1H, s) |
| 3 | 1760, 1700, 1670, 1600, 1575 | (CDCl$_3$) 3.2–3.3(1H, br), 3.79(3H, s), 4.0(3H, br), 4.7–4.8(1H, br), 4.8–4.9(1H, br), 5.02(1H, d, J=4.8Hz), 5.05–5.2(1H, br), 5.7–5.85(1H, br), 5.88(1H, dd, J=4.8Hz, 8.8Hz), 6.80(2H, d, J=8.4Hz), 7.0–7.1(2H, b), 7.2–7.35(15H, m), 7.65–7.85(15H, m) |
| 4 | 1760, 1715, 1655, 1590 | (CDCl$_3$) 3.32(1H, d, J=17Hz), 3.52(1H, d, J=17Hz), 3.81(3H, s), 4.11(2H, d, J=8.1Hz), 4.14(3H, s), 5.08(1H, d, J=4.9Hz), 5.16(2H, s), 5.74(1H, dt, J=11.4Hz, 8.1Hz), 5.96(1H, dd, J=4.9Hz, 9.2Hz), 6.25(1H, d, J=11.4Hz), 6.73(1H, d, J=9.2Hz), 6.88(2H, d, J=8.8Hz), 7.25(2H, d, J=8.8Hz), 7.24–7.4(15H, m), 7.53(1H, s) |
| 5 | 1760, 1715, | (CDCl$_3$) 3.51(1H, d, J=17.6Hz), 3.61(1H, d, J=17.6Hz), 3.81(3H, s), |

TABLE 1-continued (List of physical value)

| | Infra-red Absorption Spectrum (cm$^{-1}$, Nujol) | NMR ($\delta$) |
|---|---|---|
| | 1670, 1600, 1580 | 3.98(2H, d, J=8.4Hz), 4.18(3H, s), 5.03(1H, d, J=4.8Hz), 5.19(1H, d, J=11.7Hz), 5.25(1H, d, J=11.7Hz), 5.92(1H, dd, J=4.8Hz, 8.8Hz), 6.12(1H, dt J=8.4Hz, 15.8Hz), 6.79(1H, d, J=8.8Hz), 6.90(2H, d, J=8.8Hz), 7.00(1H, d, J=15.8Hz), 7.15–7.3(17H, m) |
| 6 | — | (DMSO-d$_6$) 1.12(3H, t, J=8Hz), 3.72(3H, s), 4.12(2H, q, J=8Hz), 4.43(2H, bs), 5.04–5.25(3H, m), 5.77(1H, dd, J=5Hz, 10Hz), 6.85(2H, d, J=8Hz), 7.1–7.4(17H, m), 8.44(1H, d, J=10Hz) |
| 7 | 1610, 1690 1710, 1760 | (DMSO-d$_6$) 1.22(3H, t, J=8Hz), 3.75(3H, s), 3.96–4.30(5H, m), 5.11(2H, s), 5.22(1H, d, J=5Hz), 5.82(1H, dd, J=5Hz, 10Hz), 6.28(1H, d, J=13Hz), 6.92(2H, d, J=8Hz), 7.2–7.5(17H, m), 9.52(1H, d, J=10Hz) |
| Example No. | | |
| 1 | 1755, 1650 1615, 1580 | (DMSO-d$_6$) 3.14(3H, s), 3.15(3H, s), 3.47(1H, d, J=17Hz), 3.65(1H, d, J=17Hz), 3.91(3H, s), 4.02(2H, s), 4.16(2H, d, J=7.7Hz), 5.04(1H, d, J=4.8Hz), 5.70(1H, dt, J=7.7Hz, 15.8Hz), 5.63(1H, dd, J=4.8Hz, 8.4Hz), 7.16(1H, d, J=15.8Hz), 7.64(1H, s), 8.14(2H, s), 8.23(1H, s), 9.51(1H, d, J=8.4Hz) |
| 2 | 1755, 1650, 1620, 1590 | (DMSO-d$_6$) 3.16(3H, s), 3.43(1H, d, J=16.9Hz), 3.57(1H, d, J=16.9Hz), 3.91(3H, s), 4.13(2H, d, J=7.7Hz), 4.31(2H, d, J=12.8Hz), 5.04(1H, d, J=4.8Hz), 5.62(1H, dd, J=4.8Hz, 8.4Hz), 5.68(1H, dd, J=7.7Hz, 15.8Hz), 5.95(2H, s), 7.19(1H, d, J=15.8Hz), 8.14(2H, s), 9.50(1H, d, J=8.4Hz) |
| 3 | 1750, 1655, 1620, 1585 | (DMSO-d$_6$) 1.8–2.2(4H, m), 2.88(3H×0.6, s), 3.06(3H×0.4, s), 3.49(1H×0.4, d, J=17.2Hz), 3.50(1H×0.6, d, J=17.2Hz), 3.64(1H, d, J=17.2Hz), 3.91(3H, s), 4.04(1H, m), 4.20(1H, m), 5.03(1H×0.6, d, J=4.8Hz), 5.04(1H×0.4, d, J=4.8Hz), 5.62(1H, m), 5.72(1H, m), 7.15(1H×0.6, d, J=15.4Hz), 7.18(1H×0.4, d, J=15.4Hz), 8.13(2H, s), 9.50(1H, d, J=8.4Hz) |
| 4 | 1755, 1655, 1590 | (DMSO-d$_6$) 2.0(6H, m), 3.4(6H, m), 3.44(1H, d, J=17.2Hz), 3.60(1H, d, J=17.2Hz), 3.87(2H, d, J=7.7Hz), 3.91(3H, s), 5.03(1H, d, J=4.8Hz), 5.6(2H, m), 7.11(1H, s), 7.14(1H, d, J=16.1Hz), 7.34(1H, s), 8.15(2H, s), 9.50(1H, d, J=8.4Hz) |
| 5 | 1760, 1670, 1630, 1595 | (DMSO-d$_6$) 2.97(4H, br), 2.99(3H, s), 3.2(4H, br), 3.47(1H, d, J=17.2Hz), 3.68(1H, d, J=17.2Hz), 3.91(3H, s), 4.07(2H, m), 5.06(1H, d, J=5.1Hz), 5.65(1H, dd, J=5.1Hz, 8.4Hz), 5.74(1H, m), 7.17(1H, d, J=15.8Hz), 8.13(2H, s), 9.51(1H, d, J=8.4Hz) |
| 6 | 1755, 1650, 1620, 1570 | (DMSO-d$_6$) 1.99(6H, m), 3.30(6H, m), 3.43(1H, d, J=16.9Hz), 3.59(1H, d, J=16.9Hz), 3.79(2H, d, J=7.3Hz), 3.91(3H, s), 5.02(1H, d, J=5.1Hz), 5.6(2H, m), 7.13(1H, d, J=15.8Hz), 8.14(2H, s), 9.49(1H, d, J=8.4Hz) |
| 7-A | 1755, 1650, 1590 | (DMSO-d$_6$) 1.85–2.0(2H, m), 2.1–2.3(2H, m), 3.05(3H, s), 3.48(1H, d, J=16.9Hz), 3.65(1H, d, J=16.9Hz), 3.91(3H, s), 4.45(1H, m), 5.06(1H, d, J=4.8Hz), 5.66(1H, dd, J=4.8Hz, 8.4Hz), 5.78(1H, m), 7.10(1H, d, J=15.4Hz), 7.3(1H, br), 8.13(2H, s), 9.51(1H, d, J=8.4Hz) |
| 7-B | 1760, 1650, 1590 | (DMSO-d$_6$) 1.85–1.95(2H, m), 2.1–2.25(2H, m), 2.94(3H, s), 3.50(1H, d, J=17.2Hz), 3.91(3H, s), 4.12(1H, m), 4.44(1H, m), 5.09(1H, d, J=5.1Hz), 5.69(1H, dd, J=5Hz, 8.4Hz), 5.88(1H, m), 7.08(1H, d, J=15.8Hz), 7.2(1H, br), 8.13(2H, s), 9.54(1H, d, J=8.4Hz) |
| 8 | 1755, 1650, 1595 | (DMSO-d$_6$) 3.05(3H, s), 3.06(3H, s), 3.45(1H, d, J=17.2Hz), 3.51(2H, s), 3.64(1H, d, J=17Hz), 3.91(3H, s), 4.15(2H, m), 5.03(1H, d, J=4.8Hz), 5.65(1H, m), 5.62(1H, dd, J=4.8Hz, 8.8Hz), 7.13(1H, d, J=15.8Hz), 8.14(2H, s), 9.51(1H, d, J=8.8Hz) |
| 9 | 1760, 1650, 1620, 1590 | (DMSO-d$_6$) 3.49(1H, d, J=16.9Hz), 3.63(1H, d, J=16.9Hz), 3.90(3H, s) 5.10(1H, d, J=5.1Hz), 5.38(2H, m), 5.72(1H, dd, J=5.1Hz, 8.4Hz), 6.09(1H, m), 7.12(1H, d, J=15.8Hz), 7.2(1H, br), 8.04(1H, dd, J=5.9Hz, 7.7Hz), 8.12(2H, s), 8.77(1H, d, J=7.7Hz), 8.91(1H, d, J=5.9Hz), 9.24(1H, s), 9.56(1H, d, J=8.4Hz) |
| 10 | 1750, 1650, 1580 | (D$_2$O) 1.98(2H, m), 2.25(2H, m) 3.09(2H, t, J=6Hz), 3.74(2H, s), 4.18(3H, s), 4.33(2H, t, J=6Hz), 5.22(2H, d, J=5Hz), 5.34(1H, d, J=5Hz), 5.93(1H, d, J=5Hz), 6.08(1H, dt, J=16Hz, 5Hz), 6.50(1H, d, J=16Hz), 6.68(1H, d, J=3Hz), 8.16(1H, d, J=3Hz) |
| 11 | 1760, 1685, 1670, 1625, 1590 | (DMSO-d$_6$) 1.24(6H, t, J=7.0Hz), 3.4–3.5(5H, m), 3.71(1H, d, J=16.1Hz), 3.90(2H, s), 3.91(3H, s), 4.1(2H, m), 5.06(1H, d, J=4.0Hz), 5.65(1H, m), 5.7(1H, m), 7.14(1H, d, J=15.0Hz), 7.70(1H, s), 8.04(1H, s), 8.12(2H, s), 9.51(1H, d, J=8.8Hz) |
| 12 | 1760, 1665, 1625, 1595 | (DMSO-d$_6$) 2.20(6H, s), 2.65(2H, t, J=5.9Hz), 3.00(6H, s), 3.33(2H, t, J=5.9Hz), 3.46(1H, d, J=17.2Hz), 3.66(1H, d, J=17.2Hz), 3.91(3H, s), 4.01(2H, d, J=7.0Hz), 5.04(1H, d, J=5.1Hz), 5.63(1H, dd, J=5.1Hz, 8.4Hz), 5.69(1H, dt, J=7.0Hz, 15.4Hz), 7.17(1H, d, J=15.4Hz), 8.12(2H, s), 9.50(1H, d, J=8.4Hz) |
| 13 | — | (D$_2$O) 3.24(6H, s), 4.21(2H, m), 4.21(3H, s), 5.40(1H, d, J=5Hz), 5.97(1H, d, J=5Hz), 6.18(1H, m), 7.13(1H, d, J=14.8Hz) |
| 14 | 1760, 1665, 1630, 1595 | (DMSO-d$_6$) 3.42(1H, d, J=17.2Hz), 3.56(1H, d, J=17.2Hz), 3.91(3H, s), 4.2(2H, m), 4.4(2H, m), 4.98(2H, s), 5.01(1H, d, J=5.1Hz), 5.18(1H, d, J=6.6Hz), 5.62(1H, dd, J=5.1Hz, 8.4Hz), 5.7–5.8(1H, m), |

TABLE 1-continued (List of physical value)

| | Infra-red Absorption Spectrum (cm$^{-1}$, Nujol) | NMR (δ) |
|---|---|---|
| | | 6.77(1H, d, J=2.9Hz), 7.05(1H, d, J=2.9Hz), 8.13(2H, s), 8.48(1H, d, J=2.9Hz), 9.49(1H, d, J=8.4Hz) |
| 15 | 1760, 1690, 1615, 1595 | (D$_2$O) 1.45(3H, t, J=7.5Hz), 3.34(3H, s), 3.35(3H, s), 3.76(1H, d, J=17Hz), 3.82(1H, d, J=17Hz), 4.14(2H, s), 4.33(1H, d, J=7.7Hz), 4.46(2H, q, J=7.5Hz), 5.38(1H, d, J=4.8Hz), 5.96(1H, d, J=4.8Hz), 6.05(1H, dt, J=7.7Hz, 15.75Hz), 7.03(1H, d, J=15.75Hz) |
| 16 | 1766, 1666, 1602, 1530 | (D$_2$O) 2.52(6H, m), 3.22(3H, s), 3.6-3.92(6H, m), 3.80(2H, m), 4.12(2H, m), 4.21(3H, s), 5.40(1H, d, J=4.5Hz), 5.98(1H, d, J=4.5Hz), 6.12(1H, m), 7.04(1H, d, J=15Hz) |
| 17 | 1760, 1720, 1660, 1620, 1595 | (D$_2$O) 2.32(3H, s), 3.30(8H, s), 3.75(1H, d, J=17Hz), 3.81(1H, d, J=17Hz), 4.19(3H, s), 4.30(2H, d, J=7.7Hz), 5.37(1H, d, J=4.8Hz), 5.95(1H, d, J=4.8Hz), 6.00(1H, dd, J=7.7Hz, 15.7Hz), 6.96(1H, d, J=15.7Hz) |
| 18-A | 1764, 1665, 1600, 1532 | (D$_2$O) 3.17(2H, m), 3.17(6H, s), 3.30(2H, m), 3.75(2H, br), 4.10(2H, m), 4.14(3H, s), 5.33(1H, d, J=4Hz), 5.90(1H, d, J=4Hz), 6.11(1H, m), 6.97(1H, d, J=15Hz) |
| 18-B | 1764, 1665, 1600, 1532 | (D$_2$O) 3.17(2H, br), 3.17(6H, s), 3.44(2H, br), 3.44(2H, br), 4.04(2H, m), 4.15(3H, s), 5.33(1H, d, J=4Hz), 5.92(1H, d, J=4Hz), 5.94(1H, m), 6.61(1H, d, J=12Hz) |
| 19 | 1760, 1685, 1655, 1590 | (DMSO-d$_6$) 3.17(3H, s), 3.20(3H, s), 3.27(1H, d, J=16.9Hz), 3.53(1H, d, J=16.9Hz), 3.91(3H, s), 3.97(2H, s), 4.05(1H, dd, J=13.9Hz, 8.1Hz), 4.20(1H, dd, J=13.9Hz, 7.1Hz), 5.06(1H, d, J=4.8Hz), 5.55-5.70(1H, m), 5.67(1H, dd, J=8.4Hz, 4.8Hz), 6.72(1H, d, J=11.4Hz), 7.61(1H, s), 8.12(1H, s), 8.12(2H, s), 9.52(1H, d, J=8.4Hz) |
| 20 | 1760, 1660, 1600 | (D$_2$O) 3.33(6H, s), 3.78(1H, d, J=17.2Hz), 3.85(1H, d, J=17.2Hz), 4.19(3H, s), 4.25~4.33(2H, m), 5.06(2H, s), 5.39(1H, d, J=4.8Hz), 5.96(1H, d, J=4.8Hz), 6.12(1H, dd, J=15.8Hz, 7.2Hz), 7.10(1H, d, J=15.8Hz) 9.25(1H, s) |
| 21 | — | (DMSO-d$_6$) 3.08(6H, s), 3.92(3H, s), 4.1~4.3(2H, m), 4.85(2H, s), 5.03(1H, d, J=5Hz), 5.62(1H, dd, J=5Hz, 10Hz), 5.7-5.9(1H, m), 7.24(1H, d, J=17Hz), 8.18(2H, s), 9.51(1H, d, J=10Hz), 9.90(1H, s) |
| 22 | 1170, 1670, 1610 | (D$_2$O) 3.08(6H, s), 3.77(1H, d, J=17.2Hz), 3.85(1H, d, J=17.2Hz), 4.06(2H, d, J=7.7Hz), 4.18(3H, s), 4.50(2H, s), 5.37(1H, d, J=4.8Hz), 5.95(1H, d, J=4.8Hz), 6.09(1H, dt, J=15.8Hz, 7.7Hz), 7.00(1H, d, J=15.8Hz), 7.57(1H, s), 7.93(1H, s) |
| 23 | 1770, 1660, 1600 | (D$_2$O) 3.14(6H, s), 3.77(1H, d, J=17.2Hz), 3.85(1H, d, J=17.2Hz), 4.14(2H, d, J=7.2Hz), 4.18(3H, s), 5.37(1H, d, J=4.7Hz), 5.95(1H, d, J=4.7Hz), 6.12(1H, dt, J=15.3Hz, 7.2Hz), 7.03(1H, d, J=15.3Hz), 8.09(1H, d, J=1.9Hz), 9.21(1H, d, J=1.9Hz) |
| 24 | 1765, 1660, 1600 | (D$_2$O) 3.10(6H, s), 3.77(1H, d, J=17.2Hz), 3.84(1H, d, J=17.2Hz), 4.10(2H, d, J=7.0Hz), 4.17(3H, s), 4.58(2H, s), 5.37(1H, d, J=4.8Hz), 5.94(1H, d, J=4.8Hz), 6.09(1H, dt, J=15.4Hz, 7.0Hz), 6.72(1H, d, J=2.6Hz), 7.02(1H, d, J=15.4Hz), 7.91(1H, d, J=2.6Hz) |
| 25 | 1770, 1660, 1600 | (D$_2$O) 3.12(3H, s), 3.77(1H, d, J=17.2Hz), 3.83(1H, d, J=17.2Hz), 4.11(2H, d, J=7.3Hz), 4.18(3H, s), 4.37(2H, s), 5.37(1H, d, J=5.0Hz), 5.95(1H, d, J=5.0Hz), 6.07(1H, dt, J=15.4Hz, 7.3Hz), 7.02(1H, d, J=15.4Hz), 7.10(1H, s) |
| 26 | 1770, 1670, 1600 | (D$_2$O) 3.08(6H, s), 3.77(1H, d, J=17.4Hz), 3.84(1H, d, J=17.4Hz), 4.07(1H, d, J=7.3Hz), 4.18(3H, s), 4.45(2H, s), 5.37(1H, d, J=4.9Hz), 6.08(1H, dt, J=15.4Hz, 7.3Hz), 6.73(1H, d, J=1.1Hz), 7.00(1H, d, J=15.4Hz), 7.74(1H, d, J=1.1Hz), 7.91(1H, s) |
| 27 | 1760, 1650, 1590 | (DMSO-d$_6$) 2.50(3H, s), 3.64(1H, d, J=17Hz), 3.91(3H, s), 4.12(2H, d, J=7Hz), 5.04(1H, d, J=5Hz), 5.36(1H, dd, J=5Hz, 8Hz), 5.70(1H, m), 7.14(2H, s), 7.20(1H, d, J=15Hz), 8.14(2H, s), 9.50(1H, d, J=8Hz) |
| 28 | 1765, 1710, 1660, 1620, 1590 | (DMSO-d$_6$) 3.11(3H, s), 3.71(1H, d, J=17Hz), 3.91(3H, s), 4.19(2H, m), 5.08(1H, d, J=5Hz), 5.68(1H, dd, J=5Hz, 8Hz), 5.80(1H, m), 7.19(1H, d, J=15Hz), 8.08(1H, s), 8.13(2H, s), 9.51(1H, d, J=8Hz), 9.60(1H, br) |
| 29 | 1755, 1650, 1585, | (DMSO-d$_6$) 3.01(3H, s), 3.91(3H, s), 4.1(2H, m), 5.03(1H, d, J=5Hz), 5.62(1H, dd, J=5Hz, 8Hz) 5.67(1H, m), 6.27(2H, s), 7.20(1H, d, J=16Hz), 8.14(2H, s), 9.49(1H, d, J=8Hz) |
| 30-A | 1765, 1660, 1595 | (DMSO-d$_6$) 2.67(3H, s), 3.02(3H, s), 3.45(1H, d, J=17Hz), 3.56(1H, d, J=17Hz), 3.91(3H, s), 4.00(1H, m), 4.20(1H, m), 5.04(1H, d, J=5Hz), 5.60(2H, m), 7.18(1H, d, J=16Hz), 8.13(2H, s), 9.51(1H, d, J=8Hz) |
| 30-B | 1760, 1650, 1590 | (DMSO-d$_6$) 2.66(3H, s), 3.01(3H, s), 3.43(1H, d, J=17Hz), 3.56(1H, d, J=17Hz), 3.91(3H, s), 4.00(1H, m), 4.20(1H, m), 5.03(1H, d, J=5Hz), 5.60(2H, m), 7.19(1H, d, J=16Hz), 8.14(2H, s), 9.49(1H, d, J=8Hz) |
| 31 | 1755, 1650, 1590 | (DMSO-d$_6$) 3.16(3H, s), 4.25(1H, m), 4.35(1H, m), 5.08(1H, d, J=5Hz), 5.65(1H, dd, J=5Hz), 5.80(1H, m), 7.24(1H, d, J=15Hz), 8.13(2H, s), 9.52(1H, d, J=8Hz) |
| 32 | 1755, 1650, 1585 | (DMSO-d$_6$) 3.01(6H, d, J=7Hz), 3.26(6H, d, J=7Hz), 3.45(1H, d, J=17Hz), 3.60(1H, d, J=17Hz), 3.91(5H, m), |

TABLE 1-continued (List of physical value)

| | Infra-red Absorption Spectrum (cm$^{-1}$, Nujol) | NMR ($\delta$) |
|---|---|---|
| | | 5.03(1H, d, J=5Hz), 5.60(2H, m), 7.16(1H, d, J=16Hz), 8.15(2H, s), 9.50(1H, d, J=8Hz) |
| 33 | 1760, 1650, 1590 | (DMSO-d$_6$) 2.27(3H, s), 2.60(2H, m), 2.70(2H, m), 2.97(3H, s), 3.30(4H, m), 3.45(1H, d, J=17Hz), 3.64(H, d, J=17Hz), 3.91(3H, s), 4.07(2H, d, J=8Hz), 5.04(1H, d, J=5Hz), 5.63(1H, dd, J=5Hz, 8Hz), 5.69(1H, m), 7.18(1H, d, J=17Hz), 8.13(2H, s) |
| 34 | 1750, 1590 | (D$_2$O) 2.84(2H, br), 3.16(3H, s), 3.80(4H, m), 4.18(3H, s), 5.37(1H, d, J=4.7Hz), 5.85(1H, d, J=4.7Hz), 5.84~6.28(1H, m), 6.68(1H, br), 7.07(1H, d, J=14.5Hz) |
| 35 | — | (D$_2$O) 2.76~3.24(4H, m), 3.12(6H, s), 3.28~3.82(4H, m), 4.14(3H, s), 5.32(1H, d, J=5Hz), 5.90(1H, d, J=5Hz), 6.07(1H, m), 6.98(1H, d, J=15.5Hz) |
| 36 | 1760, 1590 | (D$_2$O) 3.32(6H, s), 4.12(3H, s), 5.30(1H, d, J=5Hz), 5.87(1H, d, J=5Hz), 6.08(1H, m), 6.95(1H, d, J=15Hz) |
| 37 | — | (D$_2$O) 3.24(6H, s), 3.67(1H, d, J=17Hz), 3.73(1H, d, J=17Hz), 3.97(2H, s), 4.10(3H, s), 4.21(2H, d, J=7.7Hz), 5.34(1H, d, J=4.1Hz), 5.88(1H, d, J=4.1Hz), 5.97(1H, dt, J=15.4Hz, 7.7Hz), 6.95(1H, d, J=16.4Hz) |
| 38 | — | (DMSO-d$_6$) 2.26(4H, m), 3.69(4H, m), 3.91(3H, s), 4.98(2H, d, J=8Hz), 5.03(1H, d, J=4Hz), 5.62(1H, dd, J=4Hz, 8Hz), 5.66(1H, m), 7.18(1H, d, J=16Hz), 8.12(2H, s), 9.49(1H, d, J=8Hz) |

TABLE 2

Effect of the Invention (Antibacterial activities)

| Test compound Example | Test bacteria MIC (μg/ml) | | | | | |
|---|---|---|---|---|---|---|
| | Staph. aureus 209-P | Escher. coli NIHJ | Kleb Pneumoniae EK-6 | Ser. marcescens ES-75 | Morg. morganii EP-14 | Pseud. aeruginosa EP-01 |
| 1 | 0.4 | 0.05 | 0.05 | 0.1 | 0.05 | 0.8 |
| 2 | 0.2 | 0.05 | ≦0.025 | 0.1 | 0.05 | 1.56 |
| 3 | 0.2 | 0.05 | ≦0.025 | 0.1 | 0.05 | 1.56 |
| 4 | 0.4 | 0.05 | ≦0.025 | 0.1 | 0.05 | 1.56 |
| 5 | 0.2 | 0.05 | ≦0.025 | 0.1 | 0.1 | 0.8 |
| 11 | 0.2 | 0.05 | ≦0.025 | 0.1 | 0.05 | 1.56 |
| 12 | 0.4 | 0.05 | 0.05 | 0.1 | 0.1 | 1.56 |
| 14 | 0.2 | ≦0.025 | ≦0.025 | 0.05 | 0.05 | 1.56 |
| 15 | 0.2 | 0.1 | 0.05 | 0.2 | 0.05 | 1.56 |
| 16 | 0.4 | 0.1 | 0.05 | 0.2 | 0.05 | 1.56 |
| 17 | 0.4 | 0.05 | 0.05 | 0.1 | 0.1 | 1.56 |
| 18-A | 0.2 | ≦0.025 | ≦0.025 | 0.1 | 0.05 | 0.8 |
| 20 | 0.40 | ≦0.025 | ≦0.025 | 0.10 | 0.05 | 0.80 |
| 21 | 0.20 | ≦0.025 | ≦0.025 | 0.05 | ≦0.025 | 1.56 |
| 22 | 0.20 | 0.05 | 0.05 | 0.10 | 0.05 | 1.56 |
| 23 | 0.20 | ≦0.025 | ≦0.025 | 0.05 | ≦0.025 | 3.13 |
| 24 | 0.20 | ≦0.025 | ≦0.025 | 0.10 | 0.05 | 3.13 |
| 25 | 0.20 | ≦0.025 | 0.03 | 0.03 | 0.05 | 3.13 |
| 26 | 0.20 | ≦0.025 | ≦0.025 | 0.05 | ≦0.025 | 3.13 |
| 27 | 0.2 | ≦0.025 | ≦0.025 | 0.1 | 0.05 | 0.8 |
| 28 | 0.4 | 0.05 | 0.1 | 0.2 | 0.1 | 1.56 |
| 29 | 0.4 | 0.05 | 0.05 | 0.1 | 0.05 | 1.56 |
| 30-A | 0.1 | ≦0.025 | ≦0.025 | 0.05 | ≦0.025 | 0.4 |
| 30-B | 0.1 | ≦0.025 | ≦0.025 | 0.05 | 0.05 | 0.8 |
| 31 | 0.4 | 0.05 | ≦0.025 | 0.1 | 0.05 | 0.8 |
| 32 | 0.2 | ≦0.025 | ≦0.025 | 0.1 | 0.05 | 0.8 |
| 33 | 0.2 | ≦0.025 | ≦0.025 | 0.05 | ≦0.025 | 1.56 |
| 34 | 0.2 | ≦0.025 | 0.1 | 0.1 | 0.05 | 0.8 |
| 35 | 0.2 | ≦0.025 | 0.1 | 0.05 | 0.05 | 0.8 |
| 38 | 0.2 | ≦0.025 | ≦0.025 | 0.1 | 0.05 | 1.56 |

EXAMPLE 39

7β-[2-(5-Amino-1,2,4-thiadiazol-3-yl)-(Z)-2-methoxyiminoacetamide]-3-[(E)-3-[(1R-carbamoyl-2-hydroxyethyl)dimethylammonio]-1-propenyl]-3-cephem-4-carboxylate

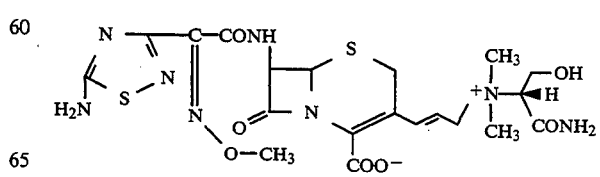

2.0 G of the compound obtained in the Experiment 5 were dissolved in 4 ml of dimethylformamide, and 319 mg of the compound obtained in the Experiment 10 were added thereto. The whole was stirred at the room temperature for one day. Ethyl ether was added thereto and the resulting precipitate was recovered and the precipitate was dissolved in a chloroform-methanol mixed solution. This solution was added to ethylether and the resulting precipitate was collected by filtration.

The precipitate was added to a mixed solution of 10 ml of trifluoroacetic acid and 10 ml of thioanisole, and the mixture was stirred for one hour under ice-cooling, followed by adding isopropylether thereto. The resulting precipitate was collected by filtration. The precipitate was suspended in water, after adjusting pH of the suspension to 7 with sodium acetate, insolubles were removed by filtration. The filtrate was purified by reversed phase silica gel column chromatography to obtain 52 mg of the objective compound.

EXAMPLE 40

7β-[2-(5-Amino-1,2,4-thiadiazol-3-yl)-(Z)-2-methoxyiminoacetamide]-3-[(E)-3-(carbamoylmethylethylmethylammonio)-1-propenyl]-3-cephem-4-carboxylate]

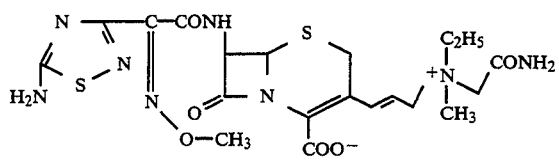

2.0 G of the compound obtained in the Experiment 5 were dissolved in 4 ml of dimethylformamide, and 280 mg of ethylmethyl aminoacetamide were added thereto. The mixture was stirred for one day at the room temperature. Ethylether was added to the mixture, and the resulting precipitate was dispensed. The dispensed precipitate was dissolved in a chloroform-methanol mixed solution. The resulting solution was added to ethylether to collect the resulting precipitate by filtration.

The precipitate was added to a mixed solution of 10 ml of trifluoroacetic acid and 10 ml of thioanisole, and the whole was stirred under ice-cooling for one hour. Isopropylether was added to the reaction liquid, and the deposited precipitates were collected by filtration. The precipitate was suspended in water, and the insolubles were removed by filtration. The filtrate was purified by an reversed phase silica gel column chromatography to obtain 46 mg of the objective compound as diastereomer mixture (1:1).

The following compound was synthesized by the same procedure as described in the Examples 30 and 40.

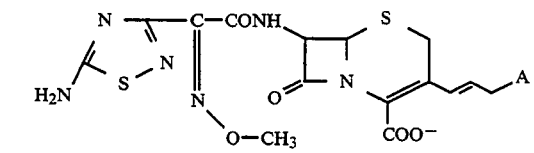

Plural number of isomers may be sometimes produced due to the portion of ammonio group of A. However, when these isomers were separated one another, the respective yields of isomers were shown.

| Example No. | A | A' (Amine) | Compound of Experiment No. 5 | Yield of the objective compound |
|---|---|---|---|---|
| 41 | —⁺N⟨⟩C(=O)CH₃(=O) (morpholinone-like) | 345 mg | 2.0 g | 19 mg |
| 42 | —N(CH₃)(CH₃)—CH(H)(CONH₂) | 280 mg | 2.0 g | 60 mg |
| 43 | —⁺N(CH₃)⟨pyrrolidine-OH, CH₂OH⟩ | 474 mg | 3.0 g | 56 mg |
| 44 | —⁺N⟨piperidine-OH, CONH₂⟩ | 415 mg | 2.0 g | Isomer (44-1) 33 mg<br>Isomer (44-2) 23 mg |
| 45 | —⁺N⟨pyrrolidine-CONH₂, OH⟩ | 568 mg | 3.0 g | Isomer (45-1) 53 mg<br>Isomer (45-2) 25 mg |

| | Infra-red Absorption Spectrum (cm$^{-1}$, Nujol) | NMR ($\delta$) |
|---|---|---|
| Experiment No. | | |
| 9 | 1610 | (DMSO-d$_6$) 0.98(3H, t, J=7.2Hz), 2.16(3H, s), 2.38(2H, q, J=7.2Hz), 2.79(2H, s), 7.03(2H, br) |
| 10 | 3350, 1670, 1025 | (DMSO-d$_6$) 2.20(6H, s), 2.78(1H, t, J=9Hz), 3.44–3.70(2H, m), 4.46(1H, br), 6.96(1H, br), 7.14(1H, br) |
| 11 | — | (DMSO-d$_6$) 1.36(3H, s), 2.05–2.9(6H, m), 3.5–4.2(4H, m) |
| Example No. | | |
| 39 | 1765, 1675, 1595 | (DMSO-d$_6$) 3.08(3H, s), 3.14(3H, s), 3.48(1H, d, J=17Hz), 3.63(1H, d, J=17Hz), 3.88(1H, dd, J=6Hz, 13Hz), 3.91(3H, s), 4.05(1H, dd, J=6Hz, 13Hz), 4.11(1H, m), 4.19(2H, d, J=7Hz), 5.06(1H, d, J=5Hz), 5.66(1H, dd, J=5Hz, 8Hz), 5.8(1H, m), 7.10(1H, d, J=15Hz), 7.76(1H, s), 8.13(2H, s), 8.48(1H, s), 9.53(1H, d, J=8Hz) |
| 40 | 1760, 1670, 1590 | (DMSO-d$_6$) 1.26(3H, t, J=7Hz), 3.08 3.09( 1H, s), 3.4–3.5(2H), 3.46(1H, d, J=17Hz), 3.65(1H, d, J=17Hz), 3.95(3H, s), 4.02(2H, s), 4.1–4.2(2H, m), 5.04(1H, d, J=5Hz), 5.63(1H, dd, J=5Hz, 8Hz), 5.69((1H, m), 7.17(1H, d, J=15Hz), 7.64(1H, s), 8.14(2H, s), 8.39(1H, s), 9.50(1H, d, J=8Hz) |
| 41 | 1750, 1650, 1590 | (DMSO-d$_6$) 1.35(9H, s), 3.91(3H, s), 4.0–4.3(2H, m), 5.04(1H, d, J=5Hz), 5.64(1H, dd, J=5Hz, 8Hz), 5.65–5.80(1H, m), 7.16(1H, d, J=16Hz), 8.12(2H, s), 9.50(1H, d, J=8Hz) |
| 42 | 1760, 1670, 1585 | (DMSO-d$_6$) 1.45(3H, d, J=7Hz), 3.03(3H, s), 3.06(3H, s), 3.49(1H, d, J=17Hz), 3.65(1H, d, J=17Hz), 3.95(3H, s), 4.03(1H, dd, J=7Hz, 13Hz), 4.2–4.4(2H, m), 5.07(1H, d, J=5Hz), 5.66(1H, dd, J=5Hz, 8Hz), 5.75(1H, m), 7.29(1H, d, J=16Hz), 7.63(1H, s), 8.12(2H, s), 8.85(1H, s), 9.50(1H, d, J=8Hz) |
| 43 | 1760, 1660, 1590 | (DMSO-d$_6$) 1.75–1.85(1H, m), 2.5–2.6(1H, m), 3.04(3H, s), 3.45(1H, d, J=17Hz), 3.66(1H, d, J=17Hz), 3.91(9H, s), 4.18(1H, m), 4.45(1H, br), 5.04(1H, d, J=5Hz), 5.62(1H, dd, J=5Hz, 8Hz), 5.72(1H, m), 7.15(1H, d, J=15Hz), 8.13(2H, s), 9.49(1H, d, J=8Hz) |
| 44-1 | 1765, 1665, 1590 | (DMSO-d$_6$) 1.85–2.05(4H, m), 2.35–2.45(1H, m), 3.2–3.4(2H, m), 3.43(1H, d, J=17Hz), 3.65(1H, d, J=17Hz), 3.8–3.85(2H, m), 3.91(3H, s), 4.11(1H, d, J=7Hz), 5.04(1H, d, J=5Hz), 5.6–5.6(1H, m), 5.62(1H, dd, J=5Hz, 8Hz), 6.99(1H, s) 7.18(1H, d, J=16Hz), 7.44(1H, s), 8.13(2H, s), 9.49(1H, d, J=8Hz) |
| 44-2 | 1760, 1660, 1590 | (DMSO-d$_6$) 1.8–2.05(4H, m), 2.3–2.5(1H, m), 3.44(1H, d, J=17Hz), 3.5–3.6(2H, m), 3.64(1H, d, J=17Hz), 3.8–3.9(2H, m), 3.91(3H, s), 4.11(1H, d, J=7Hz), 5.04(1H, d, J=5Hz), 5.63(1H, dd, J=5Hz, 8Hz), 5.70(1H, dt, J=7Hz, 16Hz), 6.95(1H, s), 7.18(1H, d, J=16Hz), 7.45(1H, s), 8.13(2H, s), 9.49(1H, d, J=8Hz) |
| 45-1 | 1760, 1680, 1590 | (DMSO-d$_6$) 1.9–2.05(1H, m), 2.35–2.5(1H, m), 3.45(1H, d, J=17Hz), 3.55–3.7(3H, m), 3.65(1H, d, J=17Hz), 3.8–3.9(1H, m), 3.91(3H, s), 4.07(2H, s), 4.20(1H, dd, J=7Hz, 13Hz), 4.32(1H, dd, J=7Hz, 13Hz), 4.51(1H, br), 5.04(1H, d, J=5Hz), 5.64(1H, dd, J=5Hz, 8Hz), 5.75(1H, m), 7.10(1H, d, J=16Hz), 7.64(1H, s), 8.13(2H, s), 8.19(1H, s), 9.59(1H, d, J=8Hz) |
| 45-2 | 1765, 1675, 1590 | (DMSO-d$_6$) 1.9–2.0(1H, m), 2.25–2.4(1H, m), 3.44(1H, d, J=17Hz), 3.6–3.8(4H, m), 3.62(1H, d, J=17Hz), 3.91(3H, s), 4.19(2H, s), 4.22(1H, d, J=8Hz), 4.50(1H, br), 5.04(1H, d, J=5Hz), 5.63(1H, dd, J=5Hz, 8Hz), 5.71(1H, dt, J=8Hz, 15Hz), 7.11(1H, d, J=15Hz), 7.65(1H, s), 8.11(1H, s), 8.13(2H, s), 9.59(1H, d, J=8Hz) |

TABLE

Effect of the Invention
Antibacterial activites

| Test compound Example | Test bacteria MIC ($\mu$g/ml) | | | | | |
|---|---|---|---|---|---|---|
| | Staph. aureus 209-P | Escher. coli NIHJ | Kleb Pneumoniae EK-6 | Ser. marcescens ES-75 | Morg. morganii EP-14 | Pseud. aeruginosa EP-01 |
| 39 | 0.4 | 0.05 | ≦0.025 | 0.1 | 0.05 | 0.8 |
| 40 | 0.2 | ≦0.025 | ≦0.025 | 0.05 | ≦0.025 | 0.8 |
| 41 | 0.4 | 0.05 | 0.05 | 0.1 | 0.05 | 1.56 |
| 42 | 0.2 | 0.05 | ≦0.025 | 0.1 | 0.05 | 0.8 |
| 43 | 0.4 | 0.05 | ≦0.025 | 0.05 | ≦0.025 | 1.56 |
| 44-1 | 0.4 | 0.05 | ≦0.025 | 0.05 | 0.05 | 0.8 |
| 44-2 | 0.4 | ≦0.025 | ≦0.025 | 0.05 | ≦0.025 | 0.8 |
| 45-1 | 0.4 | ≦0.025 | ≦0.025 | 0.05 | ≦0.025 | 0.8 |
| 45-2 | 0.4 | 0.05 | ≦0.025 | 0.05 | ≦0.025 | 0.8 |

What is claimed is:

1. A cephalosporin derivative represented by the formula:

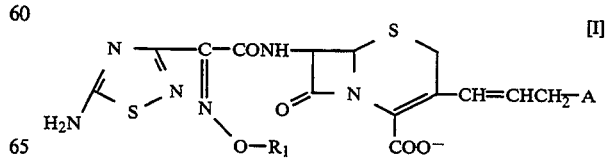

wherein $R_1$ represents a $C_{1-2}$ alkyl group, and A is a group of the formula:

an anti-bacterially effective amount of a cephalosporin derivative represented by the formula:

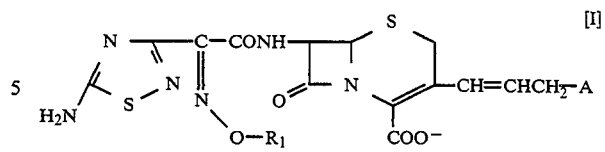

wherein $R_1$ represents a $C_{1-2}$ alkyl group, and A is a group of the formula:

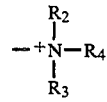

where $R_2$ and $R_3$ are the same or different $C_{1-2}$ alkyl group, and $R_4$ is a $C_{1-2}$ alkyl group substituted by a carbamoyl group, or its pharmacologically acceptable salt; and a pharmaceutically acceptable excipient.

\* \* \* \* \*

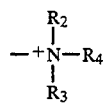

where $R_2$ and $R_3$ are the same or different $C_{1-2}$ alkyl group, and $R_4$ is a $C_{1-2}$ alkyl group substituted by a carbamoyl group, or its pharmacologically acceptable salt.

2. A cephalosporin derivative or its pharmacologically acceptable salt according to claim 1, namely 7β-[2-(5-amino-1,2,4-thiadiazol-3-yl)-(Z)-2-methoxyiminoacetamido]-3-[(E)-3-(carbamoylmethyldimethylammonio)-1-propene-1-yl]-3-cephem-4-carboxylate or its pharmacologically acceptable salt.

3. An anti-bacterial agent comprising: